US012586193B2

(12) United States Patent
Nelms et al.

(10) Patent No.: US 12,586,193 B2
(45) Date of Patent: Mar. 24, 2026

(54) TECHNIQUES FOR COMPARING IMAGE CONTOURS OF DIFFERENT HUMAN PARTICIPANTS USING AUTOMATED TOOL

(71) Applicant: Elekta, Inc., Atlanta, GA (US)

(72) Inventors: Benjamin Edward Nelms, Merrimac, WI (US); John Christodouleas, Swarthmore, PA (US)

(73) Assignee: Elekta, Inc., Atlanta, GA (US)

( * ) Notice: Subject to any disclaimer, the term of this patent is extended or adjusted under 35 U.S.C. 154(b) by 373 days.

(21) Appl. No.: 18/001,163

(22) PCT Filed: Jan. 29, 2021

(86) PCT No.: PCT/US2021/070094
§ 371 (c)(1),
(2) Date: Dec. 8, 2022

(87) PCT Pub. No.: WO2021/253020
PCT Pub. Date: Dec. 16, 2021

(65) Prior Publication Data
US 2023/0222657 A1     Jul. 13, 2023

Related U.S. Application Data

(60) Provisional application No. 63/038,081, filed on Jun. 11, 2020.

(51) Int. Cl.
*G06T 7/00* (2017.01)
*A61N 5/10* (2006.01)
(Continued)

(52) U.S. Cl.
CPC .......... *G06T 7/0014* (2013.01); *A61N 5/1031* (2013.01); *G06T 7/174* (2017.01);
(Continued)

(58) Field of Classification Search
CPC .................. G06T 7/0014; G06T 7/174; G06T 2207/20081; G06T 2207/20084;
(Continued)

(56) References Cited

U.S. PATENT DOCUMENTS 8,081,813 B2 * 12/2011 Nelms .................... G16H 20/40
378/65
12,493,960 B2 12/2025 Nelms et al.
(Continued)

FOREIGN PATENT DOCUMENTS

CN       101299965       11/2008
CN       108550156        9/2018
(Continued)

OTHER PUBLICATIONS

Xiao, Sa, et al. "Fully automated, deep learning segmentation of oxygen-induced retinopathy images." JCI insight 2.24 (2017): e97585. (Year: 2017).*

(Continued)

*Primary Examiner* — Molly Wilburn
(74) *Attorney, Agent, or Firm* — Schwegman Lundberg & Woessner, P.A.

(57)     ABSTRACT

Using a computer-implemented intermediary by which contouring performed by two participants, such as two physicians, can be compared. First, contouring performed by each participant can be compared to contouring performed by the intermediary. Then, by way of the common intermediary and a transitive analysis, contouring performed by each participant can be compared.

28 Claims, 11 Drawing Sheets

(51) Int. Cl.

| | | |
|---|---|---|
| *G06T 7/174* | (2017.01) | |
| *G16H 20/40* | (2018.01) | |
| *G16H 30/20* | (2018.01) | |
| *G16H 40/20* | (2018.01) | |

(52) U.S. Cl.
CPC ............. *G16H 20/40* (2018.01); *G16H 30/20* (2018.01); *G16H 40/20* (2018.01); *G06T 2207/20081* (2013.01); *G06T 2207/20084* (2013.01); *G06T 2207/20128* (2013.01); *G06T 2207/30056* (2013.01); *G06T 2207/30061* (2013.01); *G06T 2207/30081* (2013.01); *G06T 2207/30096* (2013.01)

(58) Field of Classification Search
CPC . G06T 2207/20128; G06T 2207/30056; G06T 2207/30061; G06T 2207/30081; G06T 2207/30096; G06T 11/80; G06T 2207/20096; G06T 2207/30004; G06T 7/12; A61N 5/1031; G16H 20/40; G16H 30/20; G16H 40/20
See application file for complete search history.

(56) References Cited

U.S. PATENT DOCUMENTS

| | | | |
|---|---|---|---|
| 2007/0280521 A1 | 12/2007 | Chao et al. | |
| 2009/0297014 A1 | 12/2009 | Nelms et al. | |
| 2014/0341449 A1 | 11/2014 | Tizhoosh et al. | |
| 2015/0238158 A1 | 8/2015 | Zhou et al. | |
| 2017/0262983 A1 | 9/2017 | Gooding et al. | |
| 2018/0308247 A1 | 10/2018 | Gupta | |
| 2019/0314644 A1* | 10/2019 | Chen ......................... | G06T 7/13 |
| 2019/0392547 A1* | 12/2019 | Katouzian .............. | G06V 20/62 |
| 2020/0160954 A1* | 5/2020 | Lyman ................... | G06N 3/084 |
| 2020/0335187 A1* | 10/2020 | Lefkofsky .............. | G16H 40/67 |
| 2023/0230670 A1 | 7/2023 | Nelms et al. | |
| 2024/0428478 A1* | 12/2024 | Gooding ............... | G06T 11/203 |

FOREIGN PATENT DOCUMENTS

| | | | | |
|---|---|---|---|---|
| CN | 110033456 | 7/2019 | | |
| CN | 116097304 | 5/2023 | | |
| GB | 2611675 | 11/2024 | | |
| WO | WO-2015176011 A1 * | 11/2015 | ........... | A61N 5/1031 |
| WO | WO-2021253020 A1 | 12/2021 | | |
| WO | WO-2021253021 A1 | 12/2021 | | |
| WO | WO-2021253022 A1 | 12/2021 | | |

OTHER PUBLICATIONS

Nelms, Benjamin E., et al. "Variations in the contouring of organs at risk: test case from a patient with oropharyngeal cancer." International Journal of Radiation Oncology* Biology* Physics 82.1 (2012): 368-378. (Year: 2012).*

Wong, Jordan, et al. "Comparing deep learning-based auto-segmentation of organs at risk and clinical target volumes to expert inter-observer variability in radiotherapy planning." Radiotherapy and Oncology 144 (2020): 152-158. (Year: 2020).*

Yang, Dong, et al. "Automatic liver segmentation using an adversarial image-to-image network." MICCAI 2017: 20th International Conference, Quebec City, QC, Canada, Sep. 11-13, 2017, Proceedings, Part III 20. Springer International Publishing, 2017. (Year: 2017).*

Gooding, Mark J., et al. "Comparative evaluation of autocontouring in clinical practice: A practical method using the Turing test." Medical physics 45.11 (2018): 5105-5115. (Year: 2018).*

U.S. Appl. No. 18/001,170, filed Dec. 8, 2022, Comparing Healthcare Provider Contours Using Automated Tool.

U.S. Appl. No. 18/001,177, filed Dec. 8, 2022, Comparing Healthcare Provider Contours Using Automated Tool.

"International Application Serial No. PCT/US2021/070094, International Search Report mailed Apr. 14, 2021", 3 pgs.

"International Application Serial No. PCT/US2021/070094, Written Opinion mailed Apr. 14, 2021", 11 pgs.

"International Application Serial No. PCT/US2021/070095, International Search Report mailed Apr. 14, 2021", 3 pgs.

"International Application Serial No. PCT/US2021/070095, Written Opinion mailed Apr. 14, 2021", 11 pgs.

"International Application Serial No. PCT/US2021/070097, International Search Report mailed Apr. 21, 2021", 4 pgs.

"International Application Serial No. PCT/US2021/070097, Written Opinion mailed Apr. 21, 2021", 8 pgs.

Nelms, Benjamin E., et al., "Variations in the contouring of organs at risk: test case from a patient with oropharyngeal cancer", International Journal of Radiation Oncology* Biology* Physics 82.1, (2012), 368-378.

Wu, Abraham J, et al., "Expert Consensus Contouring Guidelines for Intensity Modulated Radiation Therapy in Esophageal and Gastroesophageal Junction Cancer", International Journal of Radiation: Oncology Biology Physics, Pergamon Press, USA, vol. 92, No. 4, (Apr. 2, 2015), 911-920.

Xiao, SA, et al., "Fully automated, deep learning segmentation of oxygen-induced retinopathy image", JCI Insight, vol. 2, No. 24, (Dec. 21, 2017), 1-11.

"International Application Serial No. PCT US2021 070094, International Preliminary Report on Patentability mailed Dec. 22, 2022", 13 pgs.

"International Application Serial No. PCT US2021 070095, International Preliminary Report on Patentability mailed Dec. 22, 2022", 13 pgs.

"International Application Serial No. PCT US2021 070097, International Preliminary Report on Patentability mailed Dec. 22, 2022", 10 pgs.

"European Application Serial No. 21707880.7, Response to Communication Pursuant to Rules 161 and 162 filed Jun. 27, 2023", 23 pgs.

"U.S. Appl. No. 18/001,177, Non Final Office Action mailed Mar. 28, 2025", 30 pgs.

"U.S. Appl. No. 18/001,177, Notice of Allowance mailed Aug. 13, 2025", 11 pgs.

"U.S. Appl. No. 18/001,177, Corrected Notice of Allowability mailed Aug. 21, 2025", 2 pgs.

Liang, Fan, "Abdominal, multi-organ, auto-contouring method for online adaptive magnetic resonance guided radiotherapy: An intelligent, multi-level fusion approach", (2018).

"U.S. Appl. No. 18/001,177, Response filed Jun. 26, 2025 to Non Final Office Action mailed Mar. 28, 2025", 15 pages.

"Chinese Application Serial No. 202180050034.X, Office Action mailed Nov. 13, 2025", w English translation, 15 pgs.

* cited by examiner

Axial missing extra

Set 1 - - -
Set 2 ——— extra

Coronal missing

3D

Set 1 - - -
Set 2 ———

500

502
Receive first image dataset collection

504
Receive second image dataset collection

506
Auto-contour each of the first and second image datasets

508
Derive contouring comparisons of first participant vs. second participant based on analysis of their contouring vs. contouring performed by autosegmentation engine

TECHNIQUES FOR COMPARING IMAGE CONTOURS OF DIFFERENT HUMAN PARTICIPANTS USING AUTOMATED TOOL

CLAIM OF PRIORITY

This application is a U.S. National Stage Filing under 35 U.S.C. § 371 from International Application No. PCT/US2021/070094, filed on Jan. 29, 2021, and published as WO2021/253020 on Dec. 16, 2021, which claims the benefit of priority of U.S. Provisional Patent Application Ser. No. 63/038,081, titled "COMPARING CONTOURS OF SUBJECTS BY DIFFERENT PARTICIPANTS" to Benjamin Edward Nelms et al., filed on Jun. 11, 2020; the benefit of priority of each of which is hereby claimed herein, and which applications and publication are hereby incorporated herein by reference in their entireties.

FIELD OF THE DISCLOSURE

This document pertains generally to radiation therapy and more specifically, but without limitation, to a system and method for use in adaptive radiotherapy.

BACKGROUND

Radiation therapy, also known as radiotherapy, is used to treat tumors and other ailments in mammalian (e.g., human and animal) tissue. An example of a radiotherapy treatment would be the application of a high-energy beam from an external source towards a patient to produce a collimated beam of radiation directed to a target site of a patient. The target may be a region of the patient's body that contains a diseased organ or tumor that is to be exposed to, and treated by, the radiation beam. The placement and dose of the radiation beam must be accurately controlled to ensure that the target receives the dose of radiation that has been prescribed for the patient by a physician yet damage to the surrounding healthy tissue, often called the organ(s) at risk (OARs), is minimized.

To plan a patient's radiotherapy treatment one or more medical images of the patient in the intended treatment position are acquired prior to a radiation therapy (RT) treatment session and are often acquired many days before the initiation of treatment. These are referred to as planning images.

Physicians can use the planning images to identify and manually contour a target or targets as well as OARs. A treatment contour, often referred to as a planned target volume (PTV), is created which includes the target contour plus sufficient margins to account for microscopic disease as well as treatment uncertainties. A radiation dose is prescribed by the physician, and a radiation therapy treatment plan is created that optimally delivers the prescribed dose to the PTV while minimizing dose to the OARs and other normal tissues. The treatment plan can be generated manually by the physician, or can be generated automatically using an optimization technique. The optimization technique may be based on clinical and dosimetric objectives and constraints (e.g., the maximum, minimum, and mean doses of radiation to the tumor and OARs).

A treatment course is developed to deliver the prescribed dose over a number of fractions, wherein each fraction is delivered in a different treatment session. For example, 30-40 fractions are typical, but five or even one fraction can be used. Fractions are typically delivered once, or in some cases twice, per weekday. In some cases, the radiation treatment plan can change throughout the course to focus more dose in some areas. At each fraction, the patient is set up on a patient support accessory (often referred to as the "couch") of a radiation therapy device, and repositioned as closely as possible to their position in the planning images.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

SUMMARY OF THE DISCLOSURE

Figure 1:
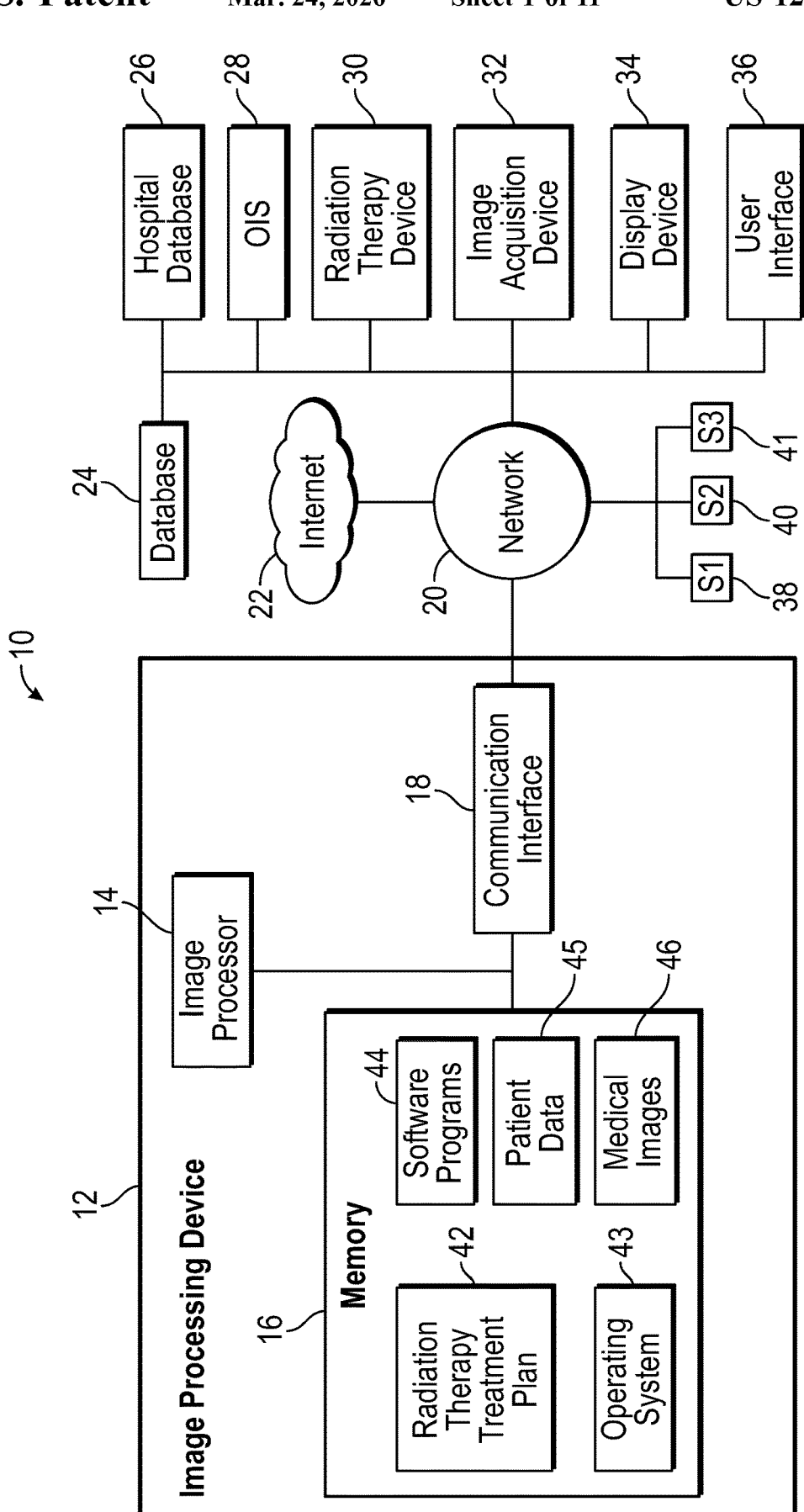
FIG. 1 illustrates an example of a radiotherapy system for providing radiation therapy to a patient with which embodiments of the disclosure may be used and/or executed.

The present inventors have recognized the desirability of using a computer-implemented intermediary by which contouring performed by two or healthcare provider participants, such as physicians or dosimetrists, can be compared. In some examples, either or both a first participant and a second participant can be a group or population of participants. First, contouring performed by each participant can be compared to contouring performed by the intermediary. Then, by way of the common intermediary and a transitive analysis, contouring performed by each participant can be compared.

In some aspects, this disclosure is directed to a computer-implemented method of comparing image contouring by different human participants without requiring that the different participants contour a shared image dataset, the method comprising: receiving a first image dataset collection, including one or more first image datasets of one or more human or animal subjects produced by an imaging modality, and including first contouring data generated by a first participant; receiving a second image dataset collection, including one or more second image datasets of one or more human or animal subjects produced by the imaging modality, including second contouring data generated by a second participant; auto-contouring each of the first and second image datasets, using a computer-implemented autosegmentation engine to obtain third contouring data generated by the autosegmentation engine without requiring human contouring and without requiring identical or overlapping first and second image datasets; and comparing contouring by the first participant to contouring by the second participant, including comparing the first contouring data generated by the first participant to the third contouring data generated by the autosegmentation engine to generate first comparison data, and also comparing the second contouring data generated by the second participant to the third contouring data generated by the autosegmentation engine to generate second comparison data.

In some aspects, this disclosure is directed to a computer-implemented system for comparing image contouring by different human participants without requiring that the different participants contour a shared image dataset, the system comprising: a computer-readable medium having instructions stored thereon, which, when executed by a processor, cause the system to: receive a first image dataset collection, including one or more first image datasets of one or more human or animal subjects produced by an imaging modality, and including first contouring data generated by a first participant; receive a second image dataset collection, including one or more second image datasets of one or more human or animal subjects produced by the imaging modality, including second contouring data generated by a second participant; auto-contour each of the first and second image datasets, using a computer-implemented autosegmentation engine to obtain third contouring data generated by the autosegmentation engine without requiring human contouring and without requiring identical or overlapping first and second image datasets; and compare contouring by the first participant to contouring by the second participant, including comparing the first contouring data generated by the first participant to the third contouring data generated by the autosegmentation engine to generate first comparison data, and also comparing the second contouring data generated by the second participant to the third contouring data generated by the autosegmentation engine to generate second comparison data.

In some aspects, this disclosure is directed to a computer-readable storage medium for comparing image contouring by different human participants without requiring that the different participants contour a shared image dataset, the computer-readable medium having instructions stored thereon, which, when executed by a processor, cause one or more machines to: receive a first image dataset collection, including one or more first image datasets of one or more human or animal subjects produced by an imaging modality, and including first contouring data generated by a first participant; receive a second image dataset collection, including one or more second image datasets of one or more human or animal subjects produced by the imaging modality, including second contouring data generated by a second participant; auto-contour each of the first and second image datasets, using a computer-implemented autosegmentation engine to obtain third contouring data generated by the autosegmentation engine without requiring human contouring and without requiring identical or overlapping first and second image datasets; and compare contouring by the first participant to contouring by the second participant, including comparing the first contouring data generated by the first participant to the third contouring data generated by the autosegmentation engine to generate first comparison data, and also comparing the second contouring data generated by the second participant to the third contouring data generated by the autosegmentation engine to generate second comparison data.

DETAILED DESCRIPTION

As mentioned above, physicians can use medical images to identify and manually contour a target or targets as well as organ(s) at risk (OARs). However, reading and interpreting medical images can be largely subjective where differences in opinion can occur across multiple, trained observers. This is especially true when it comes to accurately delineating organs or other key anatomical volumes such as tumors or other lesions or injuries.

A drive to accuracy implies a drive to consensus, which is facilitated by a comprehensive study of differences followed by negotiation until agreement is reached between experts. This process can be laborious and may need to be highly planned, with each team independently working on a large sample of common datasets, then analyzing differences and identifying trends either qualitatively and/or visually. In addition to being laborious, privacy concerns regarding patient images is an important consideration.

Consider the following scenario. Two radiation oncologists (Dr. A and Dr. C) specialize in pediatric brain cancer. They each carefully outline the radiation target volumes as well as the critical organs to spare for each and every patient using inputs of computed tomography (CT), magnetic resonance (MR), and/or positron emission tomography (PET) images. These anatomical outlines, or "contours," act as the three-dimensional (3D) blueprint to determine where to deposit (and where to avoid depositing) the radiation dose.

Dr. A and Dr. C have each contoured hundreds of different patients in practice, but they have never contoured the same patient. Neither Dr. A nor Dr. C (nor their management) know if their anatomical contouring methods are even similar, much less identical, for the different organs and volumes they delineate. If there are differences, they must be understood and, ideally, eliminated so that both physicians adopt the most accurate and consistent practice.

Dr. A and Dr. C could take on a large project of mutually contouring a common library of patients, but they are busy enough as it is, plus their management does not want to invite bias (e.g., different behavior because Dr. A and Dr. C know this set of contours will be scrutinized).

To solve the problems identified above, the present inventors have recognized the desirability of using a computer-implemented intermediary, e.g., an automated tool, by which contouring performed by two or more healthcare provider participants, such as two or more individuals (e.g., physicians or dosimetrists), one or more healthcare provider individuals and one or more groups or populations of healthcare provider participants, or two or more groups or populations of healthcare provider participants, can be compared. First, contouring performed by each participant can be compared to contouring performed by the intermediary, e.g., an automated tool. Then, by way of the common intermediary and a transitive analysis, contouring performed by each participant can be compared.

The techniques described in this disclosure can use a history of work that the participants have already done in practice. These techniques do not require the building of a controlled, cleaned, and common dataset on which they can define anatomy from scratch just for the sake of the study.

By using various techniques of this disclosure described in more detail below, meaningful feedback for each anatomical structure or sub-structure, organ, lesion, injury, among other things, can be generated based on the comparisons. For example, differences in size/volume, left/right dimension, anterior/posterior dimension, and/or superior/inferior dimension are some examples of feedback that can be generated. In some examples, the differences can be systematic.

FIG. 1 illustrates an example of a radiotherapy system 10 for providing radiation therapy to a patient with which embodiments of the disclosure may be used and/or executed. Radiotherapy system 10 includes an image processing device 12. Image processing device 12 may be connected to a network 20. Network 20 may be connected to Internet 22. Network 20 may connect image processing device 12 with one or more of a database 24, a hospital database 26, an oncology information system (OIS) 28, a radiation therapy device 30, an image acquisition device 32, a display device 34, and/or a user interface 36. Image processing device 12 may be configured to generate one or more radiation therapy treatment plans 42 to be used by radiation therapy device 30.

Image processing device 12 may include a memory 16, an image processor 14, and/or a communication interface 18. Memory 16 may store computer-executable instructions, such as an operating system 43, one or more radiation therapy treatment plans 42 (e.g., original treatment plans, and/or adapted treatment plans), software programs 44 (e.g., artificial intelligence, deep learning, neural networks, and/or radiotherapy treatment plan software), and/or any other computer-executable instructions to be executed by image processor 14. In some embodiments, software programs 44 may convert medical images of one format (e.g., MRI) to another format (e.g., CT) by producing synthetic images, such as a pseudo-CT image. For instance, software programs 44 may include image processing programs to train a predictive model for converting a medial image 46 in one modality (e.g., an MR image) into a synthetic image of a different modality (e.g., a pseudo CT image); alternatively, the trained predictive model may convert a CT image into an MRI image. Memory 16 may store data, including medical images 46, patient data 45, and/or other data required to create and/or implement radiation therapy treatment plan 42.

In addition to, or instead of, memory 16 storing software programs 44, it is contemplated that software programs 44 may be stored on a removable computer medium, such as a hard drive, a computer disk, a CD-ROM, a DVD, an HD, a Blu-Ray DVD, a USB flash drive, an SD card, a memory stick, or any other suitable medium. Software programs 44, when downloaded to image processor 14, may be executed by image processor 14.

Image processor 14 may be communicatively coupled to memory 16, and image processor 14 may be configured to execute computer-executable instructions stored thereon. Image processor 14 may send or receive medical images 46 to memory 16. For example, image processor 14 may receive medical images 46 from image acquisition device 32, or another image acquisition device, via communication interface 18 and network 18 to be stored in memory 16. Image processor 14 may also send medical images 46 stored in memory 16 via communication interface 18 to network 20 be stored in database 24 and/or hospital database 26.

Further, image processor 14 may utilize software programs 44 (e.g., treatment planning software) along with medical images 46 and/or patient data 45 to create and/or modify radiation therapy treatment plan 42. Medical images 46 may include information such as imaging data associated with a patient anatomical region, organ, or volume of interest segmentation data. The imaging data can include information about anatomical regions and organs such as, but not limited to, the lungs, liver, pelvic region, heart, and prostate. Patient data 45 may include information such as (1) functional organ modeling data (e.g., serial versus parallel organs, appropriate dose response models, etc.); (2) radiation dosage data (e.g., dose-volume histogram (DVH) information); and/or (3) other clinical information about the patient and course of treatment (e.g., other surgeries, chemotherapy, previous radiotherapy, etc.).

In addition, image processor 14 may utilize software programs to generate intermediate data, such as updated parameters to be used, for example, by a neural network model, or to generate an intermediate 2D or 3D image, which may then subsequently be stored in memory 16. Image processor 14 may then transmit executable radiation therapy treatment plan 42 via communication interface 18 to network 20 to radiation therapy device 30, which may execute radiation therapy treatment plan 42 to treat a patient with radiation. In addition, image processor 14 may execute software programs 44 to implement functions, such as, e.g., image conversion, image segmentation, deep learning, neural networks, and/or artificial intelligence. For instance, image processor 14 may execute software programs 44 that train and/or contour a medical image. Such software programs 44, when executed, may train a boundary detector and/or utilize a shape dictionary.

Image processor 14 may be a processing device, include one or more general-purpose processing devices such as a microprocessor, a central processing unit (CPU), a graphics processing unit (GPU), and/or an accelerated processing unit (APU), for example. More particularly, in some embodiments, image processor 14 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. Image processor 14 may also be implemented by one or more special-purpose processing devices, such as an application specific integrated circuit (ASIC), a field programmable gate array (FPGA), a digital signal processor (DSP), a System on a Chip (SoC), or other suitable processors. As would be appreciated by those skilled in the art, in some embodiments, image processor 14 may be a special-purpose processor, rather than a general-purpose processor. Image processor 14 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. Image processor 14 may also include graphical processing units, such as a GPU from the GeForce®, Quadro®, Tesla® family manufactured by Nvidia™, GMA, Iris™ family manufactured by Intel™, or the Radeon™ family manufactured by AMD™. Image processor 14 may also include accelerated processing units, such as the Desktop A-4(6,8) Series manufactured by AMD™, or the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein.

In addition, the term "processor" may include more than one processor, for example, a multi-core design, or a plurality of processors each having a multi-core design. Image processor 14 may be configured to execute sequences of computer program instructions, e.g., those stored in memory 16, to perform various operations, processes, and methods according to examples of the disclosure.

Memory 16 may store medical images 46. In some embodiments, medical images 46 may include, e.g., one or more MR image (e.g., 2D MRI, 3D MRI, 2D streaming MRI, 4D MRI, 4D volumetric MRI, 4D cine MRI, etc.), functional MRI images (e.g., fMRI, DCE-MRI, diffusion MRI), CT image (e.g., 2D CT, CBCT, 3D CT, 4D CT), ultrasound image (e.g., 2D ultrasound, 3D ultrasound, 4D ultrasound), PET image, X-ray image, fluoroscopic image, radiotherapy portal image, SPECT image, and/or computer-generated synthetic image (e.g., pseudo-CT images). Further, medical images 46 may include medical image data, for example, training images, ground truth images, and/or contoured images. Images stored in memory 16 may include registered and/or unregistered images, and the images may have been pre-processed or may be raw, unprocessed images. In some embodiments, medical images 46 may be received from image acquisition device 32. Accordingly, image acquisition device 32 may include an MR imaging device, a CT imaging device, a PET imaging device, an ultrasound imaging device, a fluoroscopic device, a SPECT imaging device, an integrated linac and MR imaging device, or other medical imaging devices for obtaining the medical images of the patient. Medical images 46 may be received and stored in any type of data or any type of format that image processing device 12 may use to perform operations consistent with the disclosed embodiments.

Memory 16 may be a non-transitory computer-readable medium, such as a read-only memory (ROM), a phase-change random access memory (PRAM), a static random access memory (SRAM), a flash memory, a random access memory (RAM), a dynamic random access memory (DRAM), such as synchronous DRAM (SDRAM), an electrically erasable programmable read-only memory (EE-PROM), a static memory (e.g., flash memory, flash disk, static random access memory) or any other suitable type of random access memory, e.g., a cache, a register, a compact disc read-only memory (CD-ROM), a digital versatile disc (DVD) or other optical storage, a cassette tape, other magnetic storage device, or any other non-transitory medium that may be used to store information including images, data, or computer executable instructions (e.g., stored in any format) capable of being accessed by image processor 14, or any other type of computer device. The computer program instructions may be accessed by image processor 14, read from the ROM, or any other suitable memory location, and loaded into the RAM for execution by image processor 14. For example, memory 16 may store one or more software applications. Software applications stored in memory 16 may include, for example, an operating system 43 for common computer systems, as well as for software-controlled devices. Further, memory 16 may store an entire software application, or only a part of a software application, that may be executable by image processor 14. For example, memory 16 may store one or more radiation therapy treatment plans 42.

Image processing device 12 may communicate with network 20 via communication interface 18, which may be communicatively coupled to image processor 14 and memory 16. Communication interface 18 may provide communication connections between image processing device 12 and radiotherapy system 10 components (e.g., permitting the exchange of data with external devices). For example, communication interface 18 may, in some embodiments, have appropriate interfacing circuitry to connect to user interface 36, which may be, e.g., a hardware keyboard, a keypad, and/or a touch screen through which a user may input information into radiotherapy system 10.

Communication interface 18 may include, for example, one or more of a network adaptor, a cable connector, a serial connector, a USB connector, a parallel connector, a high-speed data transmission adaptor (e.g., fiber, USB 3.0, thunderbolt), a wireless network adaptor (e.g., WiFi adaptor), a telecommunication adaptor (e.g., 3G, 4G/LTE), or other suitable interfaces. Communication interface 18 may include one or more digital and/or analog communication devices that may permit image processing device 12 to communicate with other machines and devices, such as remotely located components, via network 20.

Network 20 may provide the functionality of, for example, a local area network (LAN), a wireless network, a cloud computing environment (e.g., software as a service, platform as a service, infrastructure as a service, etc.), a client-server, or a wide area network (WAN). For example, network 20 may be a LAN or a WAN that may include other systems S1 (38), S2 (40), and S3 (41). Systems S1, S2, and S3 may be identical to image processing device 12 or may be different systems. In some embodiments, one or more systems in network 20 may form a distributed computing/simulation environment that may collaboratively perform the embodiments described herein. In some embodiments, one or more systems S1, S2, and S3 may include a CT scanner that obtains CT images (e.g., medical images 46). In addition, network 20 may be connected to Internet 22 to communicate with servers and clients that reside remotely on the Internet.

Therefore, network 20 may allow data transmission between image processing device 12 and a number of various other systems and devices, such as OIS 28, radiation therapy device 30, and/or image acquisition device 32. Further, data generated by the OIS 28 and/or image acquisition device 32 may be stored in memory 16, database 24, and/or hospital database 26. The data may be transmitted/received via network 20, through communication interface 18, in order to be accessed by image processor 14, as required.

Image processing device 12 may communicate with database 24 through network 20 to send/receive a plurality of various types of data stored on database 24. For example, database 24 may include machine data that comprises information associated with radiation therapy device 30, image acquisition device 32, and/or other machines and/or devices relevant to radiotherapy. Machine data information may include radiation beam size, arc placement, beam on and off time duration, control points, segments, MLC configuration, gantry speed, MRI pulse sequence, and/or other suitable information. Database 24 may be a storage device. One skilled in the art would appreciate that database 24 may include a plurality of devices located either in a central or a distributed manner.

In some examples, database 24 may include a processor-readable storage medium. While the processor-readable storage medium in some embodiments may be a single medium, the term "processor-readable storage medium" should be taken to include a single medium or multiple media (e.g., a centralized or distributed database, and/or associated caches and servers) that store the one or more sets of computer executable instructions or data. The term "processor-readable storage medium" shall also be taken to include any medium that is capable of storing and/or encoding a set of instructions for execution by a processor and that cause the processor to perform any one or more of the methodologies of the present disclosure. The term "processor-readable storage medium" shall accordingly be taken to include, but not be limited to, solid-state memories, optical, and magnetic media. For example, the processor-readable storage medium may be one or more volatile, non-transitory, or non-volatile tangible computer-readable media.

Image processor 14 may communicate with database 24 to read images into memory 16 and/or store images from memory 16 to database 24. For example, database 24 may be configured to store a plurality of images (e.g., 3D MRI, 4D MRI, 2D MRI slice images, CT images, 2D fluoroscopy images, X-ray images, raw data from MR scans or CT scans, Digital Imaging and Communications in Medicine (DIMCOM) data, etc.) that database 24 received from image acquisition device 32 or other image acquisition device. Database 24 may store data to be used by image processor 14 when executing software program 44, and/or when creating radiation therapy treatment plans 42. Image processing device 12 may receive medical images 46 (e.g., 2D MRI slice images, CT images, 2D fluoroscopy images, X-ray images, 3DMR images, 4D MR images, etc.) either from database 24, radiation therapy device 30 (e.g., an MRI-linac), and/or image acquisition device 32 to generate a treatment plan 42.

In an example, radiotherapy system 100 may include an image acquisition device 32 configured to acquire medical images (e.g., MR images, such as 3D MRI, 2D streaming MRI, or 4D volumetric MRI, CT images, CBCT, PET images, functional MR images (e.g., fMRI, DCE-MRI, and diffusion MRI), X-ray images, fluoroscopic images, ultrasound images, radiotherapy portal images, SPECT images, etc.) of the patient. Image acquisition device 32 may, for example, be an MR imaging device, a CT imaging device, a PET imaging device, an ultrasound device, a fluoroscopic device, a SPECT imaging device, or any other suitable medical imaging device for obtaining one or more medical images of the patient. Images acquired by imaging acquisition device 32 may be stored within database 24 as either imaging data and/or test data. By way of example, the images acquired by imaging acquisition device 32 may be also stored by image processing device 12, as medical image data 46 in memory 16.

In some embodiments, for example, image acquisition device 32 may be integrated with radiation therapy device 30 as a single apparatus (e.g., an MRI device combined with a linac, also referred to as an "MRI-linac." Such an MRI-linac may be used, for example, to determine a location of a target organ or a target tumor in the patient, so as to direct radiation therapy accurately according to radiation therapy treatment plan 42 to a predetermined target.

Image acquisition device 32 may be configured to acquire one or more images of the patient's anatomy at a region of interest (e.g., a target organ, a target tumor, or both). Each image, typically a 2D image or slice, may include one or more parameters (e.g., a 2D slice thickness, an orientation, a location, etc.). In some embodiments, image acquisition device 32 may acquire a 2D slice in any orientation. For example, an orientation of the 2D slice may include a sagittal orientation, a coronal orientation, or an axial orientation. Image processor 14 may adjust one or more parameters, such as the thickness and/or orientation of the 2D slice, to include the target organ and/or target tumor. In an exemplary embodiment, 2D slices may be determined from information, such as a 3D MRI volume. Such 2D slices may be acquired by image acquisition device 32 in "real-time" while a patient is undergoing radiation therapy treatment, for example, when using radiation therapy device 30. "Real-time" may mean acquiring the data within milliseconds (e.g., 500 milliseconds or 300 milliseconds) or less.

Image processing device 12 may generate and store radiation therapy treatment plans 42 for one or more patients. Radiation therapy treatment plans 42 may provide information about a particular radiation dose to be applied to each patient. Radiation therapy treatment plans 42 may also include other radiotherapy information, such as beam angles, dose-histogram-volume information, the number of radiation beams to be used during therapy, the dose per beam, or other suitable information or combination thereof.

Image processor 14 may generate radiation therapy treatment plans 42 by using software programs 44, for example, treatment planning software, such as Monaco®, manufactured by Elekta AB of Stockholm, Sweden. In order to generate radiation therapy treatment plans 42, image processor 14 may communicate with image acquisition device 32 (e.g., a CT device, an MRI device, a PET device, an X-ray device, an ultrasound device, etc.) to access images of the patient and to delineate a target, such as a tumor. In some embodiments, the delineation of one or more organs at risk (OARs), such as healthy tissue surrounding the tumor or in close proximity to the tumor, may be required. Therefore, segmentation of the OAR may be performed when the OAR is close to the target tumor. In addition, if the target tumor is close to the OAR (e.g., prostate in near proximity to the bladder and rectum), then by segmenting the OAR from the tumor, treatment planning device 110 may study the dose distribution not only in the target, but also in the OAR.

In order to delineate a target organ or a target tumor from the OAR, medical images, such as MR images, CT images, PET images, fMR images, X-ray images, ultrasound images, radiotherapy portal images, SPECT images, or other medical images, of the patient undergoing radiotherapy may be obtained by image acquisition device 32 to reveal the internal structure of a body part. Based on the information from the medical images, a 3D structure of the relevant anatomical portion may be obtained. In addition, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receive as low a radiation dose as possible). Other parameters that may be considered include the location of the target organ and the target tumor, the location of the OAR, and/or the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker) or automatically (e.g., using a program such as the Atlas-based auto-segmentation software, ABAS™, manufactured by Elekta AB of Stockholm, Sweden). In certain embodiments, the 3D structure of a target tumor or an OAR may be generated automatically by the treatment planning software.

After the target tumor and the OAR(s) have been located and delineated, a dosimetrist, physician, or healthcare worker may determine a dose of radiation to be applied to the target tumor, as well as any maximum amounts of dose that may be received by an OAR proximate to the tumor (e.g., left and right parotid, optic nerves, eyes, lens, inner ears, spinal cord, brain stem, or other anatomy). After the radiation dose is determined for relevant anatomical structures (e.g., target tumor, OAR), a process known as inverse planning may be performed to determine one or more treatment plan parameters that would achieve the desired radiation dose distribution. Examples of treatment plan parameters include volume delineation parameters (e.g., which define target volumes, contour sensitive structures, etc.), margins around the target tumor and OARs, beam angle selection, collimator settings, and/or beam-on times.

During the inverse-planning process, the physician may define dose constraint parameters that set bounds on how much radiation an OAR may receive (e.g., defining full dose to the tumor target and zero dose to any OAR; defining 95% of dose to the target tumor; defining that the spinal cord, brain stem, and optic structures receive ≤45 Gy, ≤55 Gy, and <54 Gy, respectively). The result of inverse planning may constitute a radiation therapy treatment plan 42 that may be stored in memory 16 or database 24. Some of these treatment parameters may be correlated. For example, tuning one parameter (e.g., weights for different objectives, such as increasing the dose to the target tumor) in an attempt to change the treatment plan may affect at least one other parameter, which in turn may result in the development of a different treatment plan. Thus, image processing device 12 may generate a tailored radiation therapy treatment plan 42 having these parameters in order for radiation therapy device 30 to provide radiotherapy treatment to the patient.

In addition, radiotherapy system 10 may include a display device 34 and a user interface 36. Display device 34 may include one or more display screens configured to display medical images, interface information, treatment planning parameters (e.g., contours, dosages, beam angles, etc.) treatment plans, a target, localizing a target and/or tracking a target, or any suitable information to the user. User interface 36 may be a keyboard, a keypad, a touch screen, or any type of device that a user may input information to radiotherapy system 10. Alternatively, display device 34 and user interface 36 may be integrated into a device such as a smart phone, computer, or tablet computer, e.g., Apple iPad®, Lenovo Thinkpad®, Samsung Galaxy, etc.

Furthermore, any and all components of radiotherapy system 10 may be implemented as a virtual machine (e.g., VMWare, Hyper-V, etc.). For example, a virtual machine may be software that functions as hardware. Therefore, a virtual machine may include at least one or more virtual processors, one or more virtual memories, and/or one or more virtual communication interfaces that together function as hardware. For example, image processing device 12, OIS 28, and/or image acquisition device 32 may be implemented as a virtual machine. Given the processing power, memory, and computational capability available, the entire radiotherapy system 10 may be implemented as a virtual machine.

Figure 2:
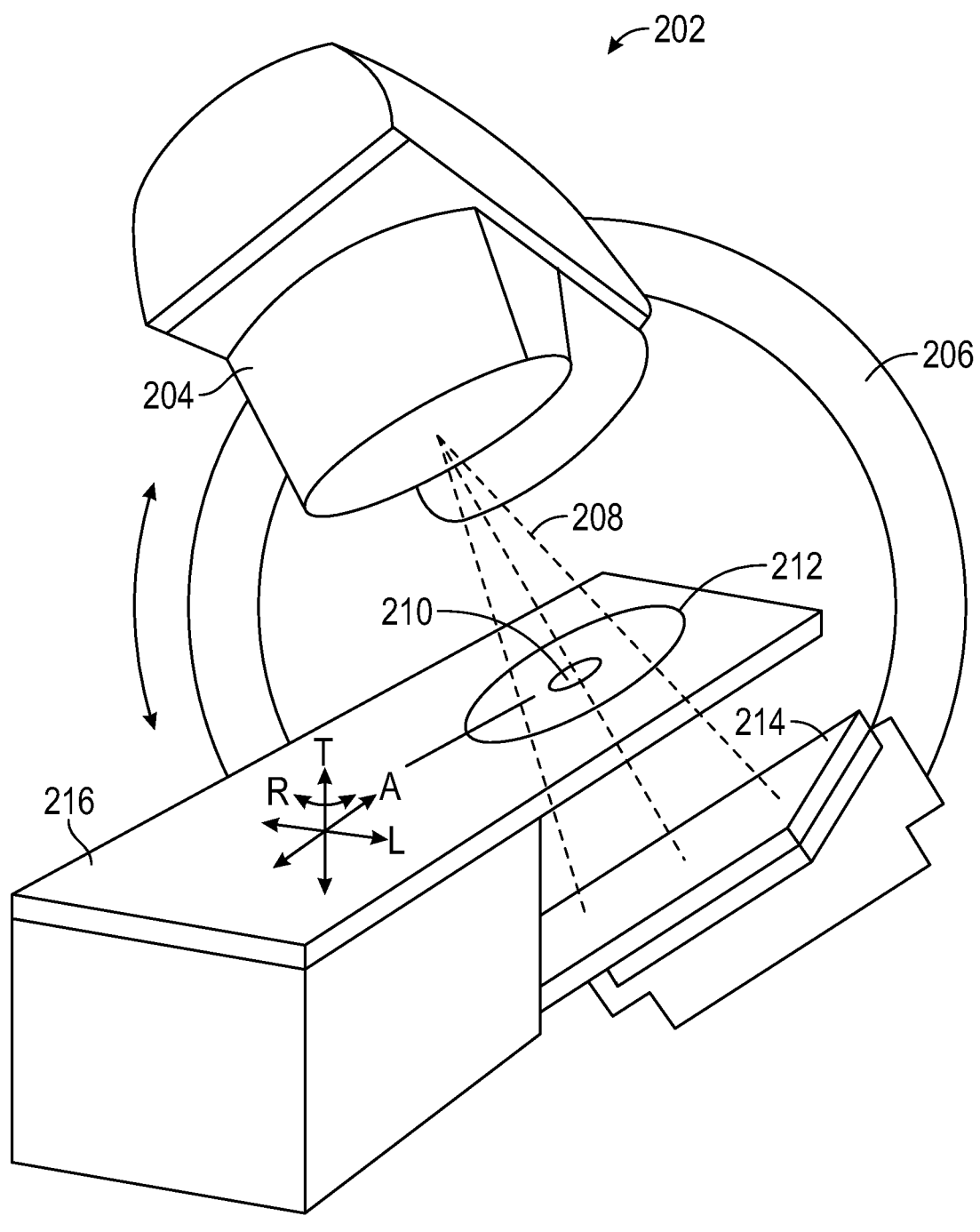
FIG. 2 illustrates an example of a radiation therapy system that may include a radiation therapy output configured to provide a therapy beam.

FIG. 2 illustrates an example of a radiation therapy device 202 that may include a radiation source, such as an X-ray source or a linear accelerator, a couch 216, an imaging detector 214, and a radiation therapy output 204. The radiation therapy device 202 may be configured to emit a radiation beam 208 to provide therapy to a patient. The radiation therapy output 204 may include one or more attenuators or collimators, such as a multi-leaf collimator (MLC).

Referring back to FIG. 2, a patient may be positioned in a region 212, supported by the treatment couch 216 to receive a radiation therapy dose according to a radiation therapy treatment plan. The radiation therapy output 204 may be mounted or attached to a gantry 206 or other mechanical support. One or more chassis motors (not shown) may rotate the gantry 206 and the radiation therapy output 204 around couch 216 when the couch 216 is inserted into the treatment area. In an embodiment, gantry 206 may be continuously rotatable around couch 216 when the couch 216 is inserted into the treatment area. In another embodiment, gantry 206 may rotate to a predetermined position when the couch 216 is inserted into the treatment area. For example, the gantry 206 may be configured to rotate the therapy output 204 around an axis ("A").

Both the couch 216 and the radiation therapy output 204 may be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216 movements or rotations in order to properly position the patient in or out of the radiation beam 208 according to a radiation therapy treatment plan. As both the couch 216 and the gantry 206 are independently moveable from one another in multiple degrees of freedom, which allows the patient to be positioned such that the radiation beam 208 precisely can target the tumor.

The coordinate system (including axes A, T, and L) shown in FIG. 2 may have an origin located at an isocenter 210. The isocenter 210 may be defined as a location where the central axis of the radiation therapy beam 208 intersects the origin of a coordinate axis, such as to deliver a prescribed radiation dose to a location on or within a patient. Alternatively, the isocenter 210 may be defined as a location where the central axis of the radiation therapy beam 208 intersects the patient for various rotational positions of the radiation therapy output 204 as positioned by the gantry 206 around the axis A.

Gantry 206 may also have an attached imaging detector 214. The imaging detector 214 preferably located opposite to the radiation source 204, and in an embodiment, the imaging detector 214 may be located within a field of the therapy beam 208.

The imaging detector 214 may be mounted on the gantry 206 preferably opposite the radiation therapy output 204, such as to maintain alignment with the therapy beam 208. The imaging detector 214 rotating about the rotational axis as the gantry 206 rotates. In an embodiment, the imaging detector 214 may be a flat panel detector (e.g., a direct detector or a scintillator detector). In this manner, the imaging detector 214 may be used to monitor the therapy beam 208 or the imaging detector 214 may be used for imaging the patient's anatomy, such as portal imaging. The control circuitry of radiotherapy device 202 may be integrated within system 100 or remote from it.

In an illustrative embodiment, one or more of the couch 216, the therapy output 204, or the gantry 206 may be automatically positioned, and the therapy output 204 may establish the therapy beam 208 according to a specified dose for a particular therapy delivery instance. A sequence of therapy deliveries may be specified according to a radiation therapy treatment plan, such as using one or more different orientations or locations of the gantry 206, couch 216, or therapy output 204. The therapy deliveries may occur sequentially, but may intersect in a desired therapy locus on or within the patient, such as at the isocenter 210. A prescribed cumulative dose of radiation therapy may thereby be delivered to the therapy locus while damage to tissue nearby the therapy locus may be reduced or avoided.

As mentioned above, the present inventors have recognized the desirability of using a computer-implemented intermediary by which contouring performed by two participants, such as two individuals, e.g., physicians, can be compared. In some examples, either or both the first participant and the second participant can be a group or population of participants. First, contouring performed by each participant can be compared to contouring performed by the intermediary. Then, by way of the common intermediary and a transitive analysis, contouring performed by each participant can be compared. A conceptual illustration is presented in FIG. 3.

Figure 3:
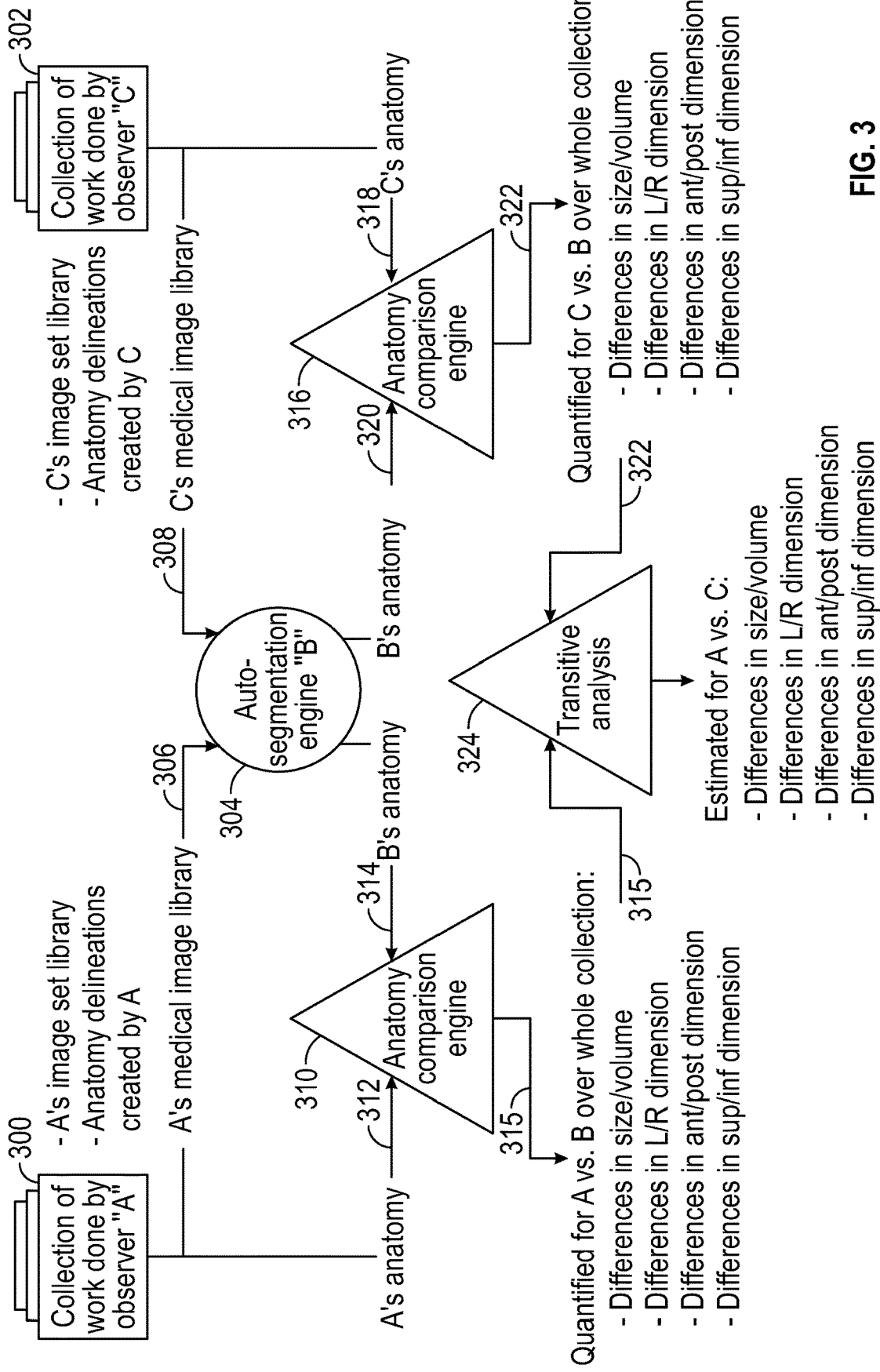
FIG. 3 is a conceptual diagram illustrating the use of a computer-implemented autosegmentation engine that can compare image contouring by two or more different healthcare provider participants without requiring that the different participants contour a shared image dataset, in accordance with various techniques of this disclosure.

FIG. 3 is a conceptual diagram illustrating the use of a computer-implemented autosegmentation engine that can compare image contouring by two or more different healthcare provider participants without requiring that the different participants contour a shared image dataset. Two image dataset collections are shown in FIG. 3: a first image dataset collection 300 and second image dataset collection 302. Each image dataset collection can include one or more image datasets of one or more human or animal subjects produced by an imaging modality, such as CT, MR and/or PET images, and including contouring data generated by the corresponding healthcare provider participant, e.g., participant A or participant C, or healthcare provider participant generated contouring data. The participants can be individuals, such as physicians or dosimetrists, or a group or population of participants.

The first image dataset collection 300 can include a collection of work done by observer or participant A, such as participant A's image set library, and the contouring or delineations created by participant A, and the second image dataset collection 302 can include a collection of work done by observer or participant C, such as participant C's image set library, and the contouring or delineations created by participant C. The contouring or delineations can include anatomical structures or sub-structures, organs, lesions, and/or injuries, for example.

In some examples, at least one of the first image dataset collection 300 and the second image dataset collection 302 can include metadata, in addition to the human participant generated contouring data. The metadata can be provided as an input to the autosegmentation engine 304.

The metadata can include at least one of the following: an indication of at least one imaging modality type or other imaging modality parameter used to generate images in a corresponding image dataset; an indication of a characteristic of an organ or other target structure to be targeted for treatment; an indication of a characteristic of an organ or other structure at risk to be avoided for treatment; an indication of a characteristic of a patient demographic of the human or animal subject corresponding to images in a corresponding image dataset; an indication of a disease characteristic associated with the human or animal subject corresponding to images in a corresponding image dataset; an indication of a treatment characteristic associated with the human or animal subject corresponding to images in a corresponding image dataset; and an indication of a desired treatment outcome associated with the human or animal subject corresponding to images in a corresponding image dataset.

Each observer or participant can provide a sufficient collection of patient datasets that they have already processed, e.g., an anonymized sampling of their past patients. Each image dataset collection can include, for example, a series of images comprising a patient volume, such as a series of axial Digital Imaging and Communications in Medicine (DICOM) images, a specific imaging modality (e.g., CT, MR, and/or PET images), and/or a standard set of anatomy contoured on each image set (e.g., provided as a DICOM RT structure set).

Each image dataset collection can represent a specific combination of imaging modality (e.g., CT, MR, and/or PET images), body site, and a set of anatomical volumes, for example.

A computer-implemented autosegmentation engine 304 (autosegmentation engine "B") can receive the first image dataset collection 300, including one or more first image datasets of one or more human or animal subjects produced by an imaging modality, and including first contouring data generated by the first participant A. For example, as shown in FIG. 3, the autosegmentation engine 304 can receive A's contoured medical image library (shown as input 306).

The autosegmentation engine 304 can be a computer program that receives as input an image set and generates anatomical contours for a set of anatomical structures and substructures, such as a substructure of a heart, organs, lesions, and injuries with no user intervention. The autosegmentation engine 304 does not have to be 100% accurate nor does it need to agree with any or all observers. However, it is desirable that the autosegmentation engine 304 be robust and consistent in its behavior across many different image sets of the same imaging modality and body site. In some example, the autosegmentation engine 304 can be a previously trained machine learning model that was trained using a library of high-quality image and structure set examples.

Similarly, the computer-implemented autosegmentation engine 304 (autosegmentation engine "B") can receive the second image dataset collection 302, including one or more second image datasets of one or more human or animal subjects produced by the imaging modality, including second contouring data generated by the second participant B. For example, as shown in FIG. 3, the autosegmentation engine 304 can receive B's contoured medical image library (shown as input 308).

Without requiring human contouring and without requiring identical or overlapping first and second image datasets, the computer-implemented autosegmentation engine 304 can then auto-contour each of the first and second image datasets received from participants A and B, to obtain third contouring data generated by the autosegmentation engine. In some examples, the first and second image datasets can overlap.

In some examples, the autosegmentation engine 304 can be configured to perform the auto-contouring by including or using an atlas-based model. In some examples, the autosegmentation engine 304 can be configured to perform the auto-contouring by including or using a trained model. For example, the trained model can be trained using at least one or more of statistical learning, artificial intelligence, machine learning, neural networks, generative adversarial network, or deep learning. The model can be trained independently using a different and independent learning image dataset. In some examples, the different and independent learning image dataset can include images from a population of human or animal subjects overlapping with at least one of the one or more first and second image datasets from the human or animal subjects.

A computer-implemented first anatomy comparison engine 310 can compare the first contouring data generated by the first participant A (shown as input 312) to the third contouring data generated by the autosegmentation engine 304 (shown as input 314) to generate first comparison data 315. The first comparison data 315 can provide meaningful feedback for each anatomical structure, organ, lesion, injury, etc. For example, between the participant A and the auto-contouring performed by the autosegmentation engine 304, differences, e.g., systematic differences, in size/volume, left/right dimension, anterior/posterior dimension, and/or superior/inferior dimension can be generated based on the first comparison data.

In some examples, comparing the first contouring data generated by the first participant A to the third contouring data generated by the autosegmentation engine 304 can include voxel analysis of a human-contoured region compared to an auto-contoured region. For example, the voxel analysis can include analyzing a distance between (1) one or more unmatched voxels, between the human-contoured region and an auto-contoured region, and (2) a closest voxel location matched between the human-contoured region and the auto-contoured region. In some examples, a quality metric can be generated based on the analyzed distance.

As another example, the voxel analysis can alternatively or additionally include analyzing a direction between (1) one or more unmatched voxels, between the human-contoured region and an auto-contoured region, and (2) a closest voxel location matched between the human-contoured region and the auto-contoured region. In some examples, a quality metric can be generated based on the analyzed direction.

In some examples, the voxel analysis can include generating a statistical representation of difference vectors between (1) one or more unmatched voxels, between the human-contoured region and an auto-contoured region, and (2) a closest voxel location matched between the human-contoured region and the auto-contoured region. In some examples, a quality metric can be generated based on the statistical representation of difference vectors.

The first comparison data 315 can provide meaningful feedback for each anatomical structure or sub-structure, organ, lesion, injury, etc. For example, between the participant A and the auto-contouring performed by the autosegmentation engine 304, differences in size/volume, left/right dimension, anterior/posterior dimension, and/or superior/inferior dimension can be generated based on the first comparison data 315. In some examples, the differences can be systematic.

Similarly, a computer-implemented second anatomy comparison engine 316 can compare the second contouring data generated by the second participant C (shown as input 318) to the third contouring data generated by the autosegmentation engine (shown as input 320) to generate second comparison data 322. In some examples, comparing the second contouring data generated by the second participant C to the third contouring data generated by the autosegmentation engine 304 can include voxel analysis of a human-contoured region compared to an auto-contoured region.

In some examples, the first anatomy comparison engine 310 and the second anatomy comparison engine 316 can be the same engine.

The second comparison data 322 can provide meaningful feedback for each anatomical structure or sub-structure, organ, lesion, injury, etc. For example, between the participant B and the auto-contouring performed by the autoseg-mentation engine 304, systematic differences in size/volume, left/right dimension, anterior/posterior dimension, and/ or superior/inferior dimension are some examples of feedback that can be generated based on the second comparison data 322.

The computer-implemented first and second anatomy comparison engines 310, 316 can be a computer program that can perform comprehensive 3D analysis of any two collections of anatomy structure sets for common image sets, for example. As an example, an anatomy comparison engine can perform voxelization of contoured anatomy into sufficiently high-resolution volume elements (e.g., 0.001 cc, or 1 mm per side) and analysis of all matching (common), missing, and extra voxels in the first set versus the second set.

The anatomy comparison engines 310, 316 can perform a per voxel determination of difference vectors that are 3D "vector-to-agreement" lines connecting un-matched (missing or extra) voxels to the closest point on the surface of the other volume. In some examples, a difference distance is the total length of a difference vector. Matching voxels can have 0 mm difference, missing voxels can have a negative difference distance based on how far away they are from the other set's surface, and extra voxels can have a positive difference distance.

The comparison can yield, for each anatomic volume in each dataset, the following: 1) comparisons of absolute volume (e.g., size); 2) distribution of missing, matching, and extra volume for set 1 vs. set 2 as a histogram of contoured volume versus difference distance; 3) histogram of the x-component (usually patient L-R) of the difference vectors, as well as mean and standard deviation of the differences in that dimension; 4) histogram of the y-component (usually patient superior-inferior) of the difference vectors, as well as mean and standard deviation of the differences in that dimension; and/or 5) histogram of the z-component (usually patient anterior-posterior) of the difference vectors, as well as mean and standard deviation of the differences in that dimension.

Comparison can be presented using a user interface, such as shown and described below with respect to FIGS. 9 and 10.

In some examples, comparisons can be repeated for all datasets in the collection and the results and statistics tallied into distributions of results (e.g., across all datasets) to determine if differences are significant using analysis of variance (ANOVA) techniques versus null hypothesis (no significant differences), and determine if differences are systematic or random.

It should be noted that the anatomy comparison engines 310, 316 can work directly for any plurality of participants or observers who contour a common library of image sets. However, the techniques of this disclosure can compare image contouring by different human participants without requiring that the different participants contour a shared image dataset.

Finally, the computer-implemented techniques of this disclosure can compare the contouring by the first participant to contouring by the second participant by performing a transitive analysis comparison of the contouring by the first and second participants by comparing each to a reference provided by the third contouring data generated by the autosegmentation engine. For example, a computer-implemented transitive engine p can, using a transitive property, compare contouring by the first participant A to contouring by the second participant B. The computer-implemented transitive engine 324 can be a computer program that can perform comprehensive 3D analysis of datasets. For example, the computer-implemented transitive engine 324 can compare the first comparison data 315 and the second comparison data 322 to determine statistically significant trends in systematic differences in size/volume, left/right dimension, anterior/posterior dimension, and/or superior/inferior dimension between the first participant A and the second participant B.

As mentioned above, the first and/or second participants can be a group or population of participants, such as physicians. Thus, in some examples, comparing contouring by the first participant A to contouring by the second participant C can include comparing contouring by the first participant A to individual or aggregated contouring by a group or population of second participants C. In some examples, comparing contouring by the first participant to contouring by the second participant can include comparing individual or aggregated contouring by a group or population of first participants to individual or aggregated contouring by a group or population of second participants.

It should be noted that although the techniques are described as comparing contouring by the first participant A to contouring by the second participant C, the techniques of this disclosure are not limited to first and second participants. Rather, the techniques of this disclosure can be iterated to compare the second participant C to a third participant D, or further iterated to extend to one or more further participants. In some examples, the comparison can be performed on cloud-based anonymized image datasets, and a result based on the comparing can be delivered in a cloud-based location. For example, a computer server device, such as the computer server device 602 of FIG. 8, can automatically anonymize the image datasets, such as after the image datasets are uploaded to the computer server device.

In some examples, based on the comparison between contouring by the first participant A to contouring by the second participant C, the transitive engine 324 can generate a quality metric. The transitive engine 324 can generate the quality metric regardless of whether contouring was performed by individual participants, performed by an individual participant and a group or population of participants, or performed by two groups or populations of participants.

The quality metric can include contouring information correlated with at least one of treatment plan information, treatment safety information, treatment efficacy information, or treatment outcome information about one or more treatments carried out using the contouring information. In some examples, at least one of treatment safety information, efficacy information, or outcome information can include toxicity information, including at least one of a toxicity indication, a toxicity prediction, or a toxicity risk indication. At least one of treatment safety information, efficacy information, or outcome information can include toxicity information localized to an anatomical structure, sub-structure, or region.

In some examples, the computer-implemented method described in this disclosure can include selecting healthcare provider participants for contouring in a clinical study on human or animal subjects based at least in part on the quality metric. For example, healthcare provider participants, such as physicians or dosimetrists, can be associated with at least one of hospital affiliation, physician practice group affiliation, or geographic location.

The individual or aggregated contouring by a group or population of second participants, for example, can provide a gold standard benchmark against which the individual or aggregated contouring by the group or population of the first participants is compared.

In some examples, the transitive engine 324 can generate an indication of one or more of the systematic differences between contouring by the first and second participants. In some examples, the transitive engine 324, for example, can normalize the indication of the systematic difference with respect to a parameter based upon a contour generated by the autosegmentation engine. Among other things, the parameter can include a volume or size dimension, e.g., 20% larger, and/or one or more directional dimensions including, but not limited to, left/right, superior/inferior, and/or anterior/posterior.

For example, the transitive engine 324 can generate an indication an indication of a systematic difference in a contoured volume. As another example, the transitive engine 324 can generate an indication of a systematic difference in a lateral contoured dimension. In some examples, the transitive engine 324 can generate an indication of a systematic difference in an anterior or posterior contoured dimension.

In some examples, the transitive engine 324 can generate an indication of a systematic difference in a superior or inferior contoured dimension. The contoured volume or dimension can include at least one of a contoured organ volume or dimension, a contoured organ substructure volume or dimension, a contoured anatomical structure volume or dimension, or an injured or diseased region structure volume or dimension.

The transitive engine 324 can, for example, perform dataset-by-dataset comparisons over the entire population of participant A versus the autosegmentation engine 304 ("B") and participant C. The transitive engine 324 can receive systematic trends computed for participant A versus autosegmentation engine 304 ("B") (e.g., via the first comparison data 315) and systematic trends computed for participant C versus autosegmentation engine (e.g., via the second comparison data 320). Using the common autosegmentation engine 304 ("B") as the intermediary, the transitive engine 324 can determine statistically significant trends of or differences between participant A versus participant C.

As described above, FIG. 3 graphically depicts a computer-implemented method that uses a computer-implemented autosegmentation engine to auto-contour two image datasets, for example, where each of the image datasets was previously contoured by a corresponding participant, such as a physician. Then, the computer-implemented method can compare contouring performed by the first participant, such as a first physician (Dr. A), to contouring performed by the second participant, e.g., such as a second physician (Dr. C). For example, the computer-implemented method can compare the contouring data generated by the first participant to the contouring data generated by the autosegmentation engine to generate first comparison data, and also compare the contouring data generated by the second participant to the contouring data generated by the autosegmentation engine to generate second comparison data.

Using the first comparison data, the computer-implemented method can identify systematic trends between the contouring data generated by the first participant to the contouring data generated by the autosegmentation engine and systematic trends between the contouring data generated by the second participant to the contouring data generated by the autosegmentation engine. Then, using the common contouring data generated by the autosegmentation engine, systematic trends between the contouring data generated by the first and second participants can be determined.

Figure 6:
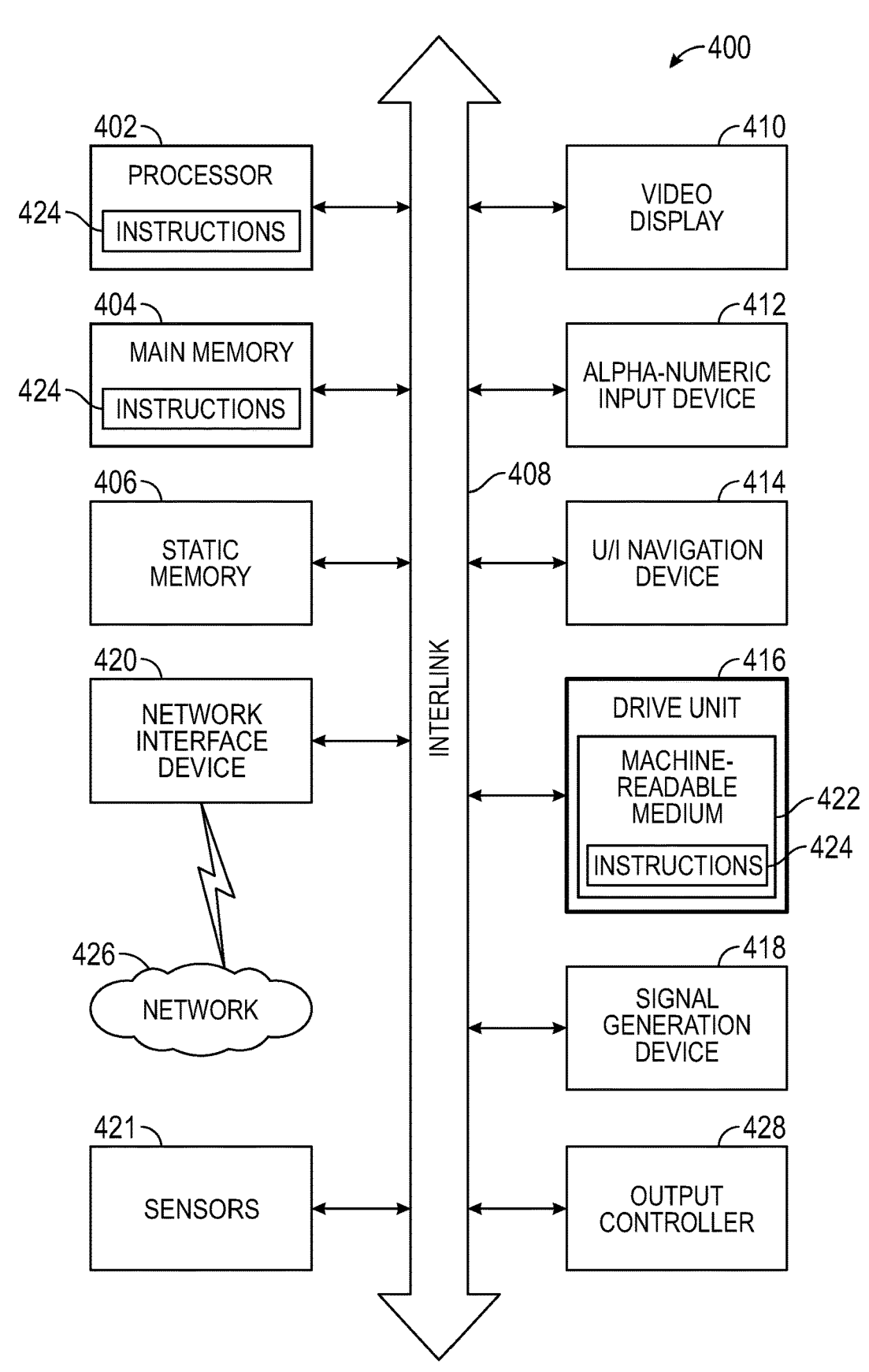
FIG. 6 illustrates a block diagram of an example of a machine upon which any one or more of the techniques (e.g., methodologies) discussed herein can perform.

The engines described in this disclosure, such as the autosegmentation engine 304, the anatomy comparison engines 310, 316, and the transitive engine 324 can be implemented using the machine 400 of FIG. 6. For example, one or more of the autosegmentation engine 304, the anatomy comparison engines 310, 316, and the transitive engine 324 can be implemented using instructions 424 that are executed by the processor 402. In some examples, the autosegmentation engine 304, the anatomy comparison engines 310, 316, and the transitive engine 324 can be the same engine. The autosegmentation engine 304, the anatomy comparison engines 310, 316, and the transitive engine 324 can be co-located on one machine or located in different machines.

Figure 4A:
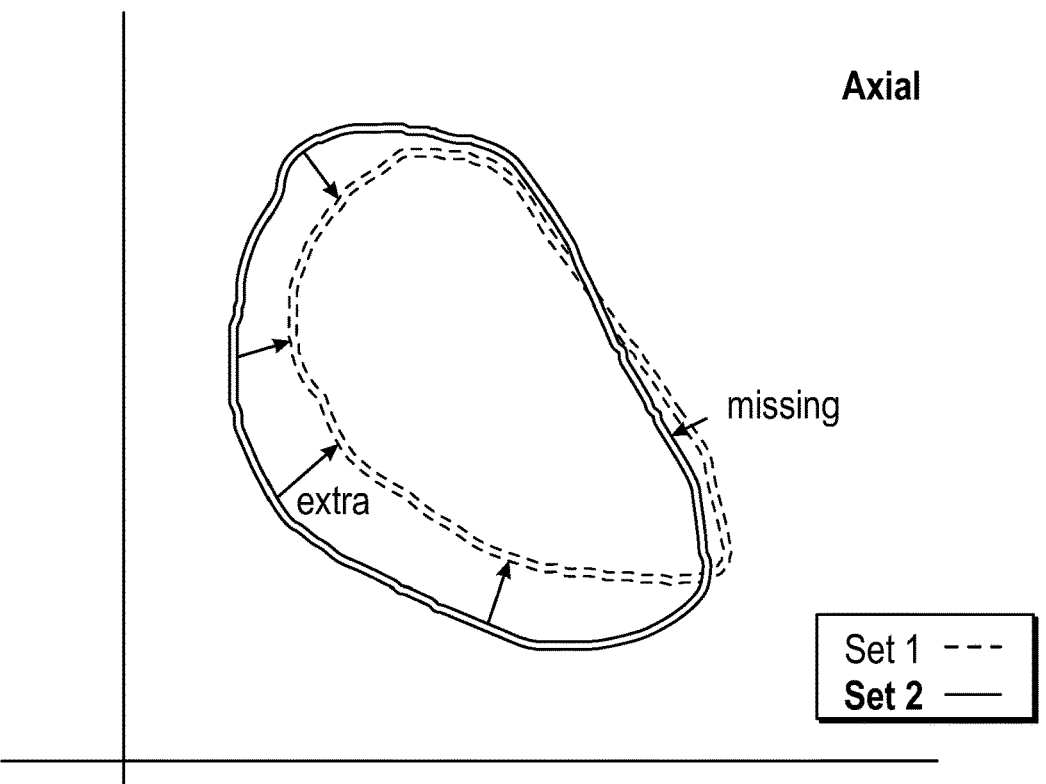
FIGS. 4A and 4B are graphical representations of a comparison between two image datasets.
Figure 4B:
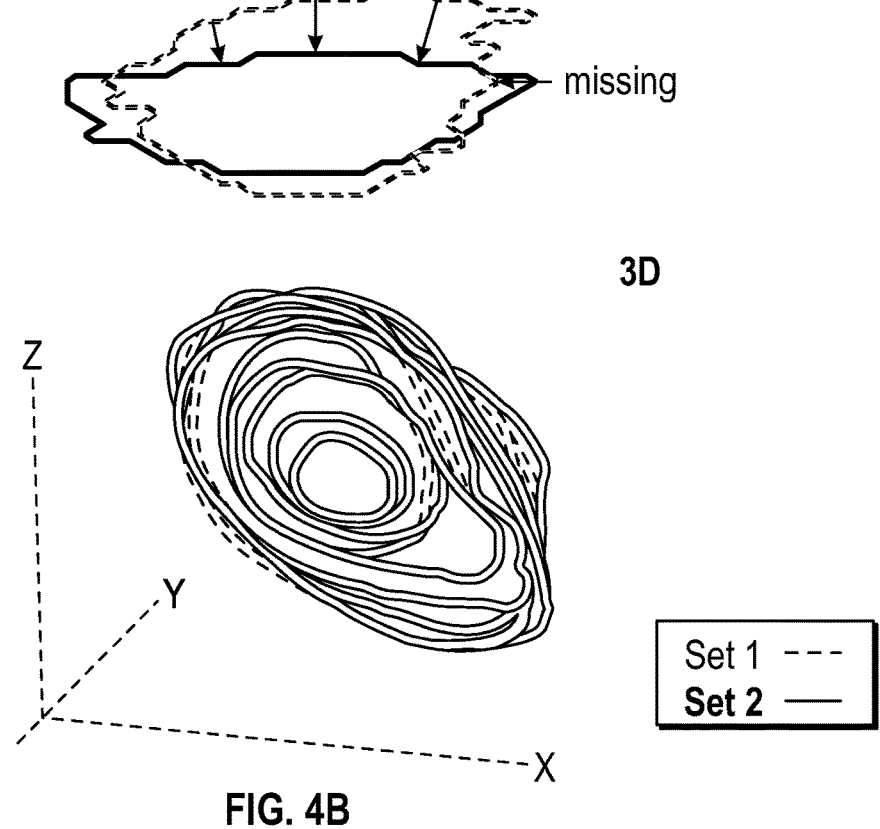

FIGS. 4A and 4B are graphical representations of a comparison between two image datasets. FIG. 4A depicts an axial view of the contouring of the two image datasets and FIG. 4B depicts a coronal view of the contouring of the two image datasets.

In some examples, to perform a comparison, an anatomy comparison engine, such as the anatomy comparison engines 310, 316 of FIG. 3, can voxelize a specific contoured structure from both Set 1 and Set 2 to a common, high-resolution 3D grid, and analyze each voxel in the grid.

If the voxel is in both structures, it is a matching voxel and the distance difference vector is zero length in all dimensions. The anatomy comparison engine can tally the voxel as a matching voxel.

If the voxel is in Set 2 but not Set 1, the voxel is an extra voxel (e.g., Set 2 had the voxel but Set 1 did not). The anatomy comparison engine can compute the 3D difference vector (3D) from the voxel to the closest point on the surface of Set 1. The anatomy comparison engine can tally the distance (e.g., the sign is positive) and break into directional components in X, Y, and Z coordinates.

If the voxel is not in Set 2 but is in Set 1, the voxel is a missing voxel (e.g., Set 2 did not have the voxel but Set 1 did). The anatomy comparison engine can compute the 3D difference vector (3D) from the voxel to the closest point on the surface of Set 1. The anatomy comparison engine can tally the distance (e.g., the sign is negative) and break into directional components in X, Y, and Z coordinates.

Using these techniques, the anatomy comparison engine can accumulate histograms of the lengths of the difference vectors and 3D components, with signs. In addition, the anatomy comparison engine can compute basic metrics (e.g., absolute volumes and Dice coefficient) for similarity comparisons.

FIGS. 5A-5D depict examples of graphs comparing the two image datasets depicted in FIGS. 4A-4B.

Figure 5A:
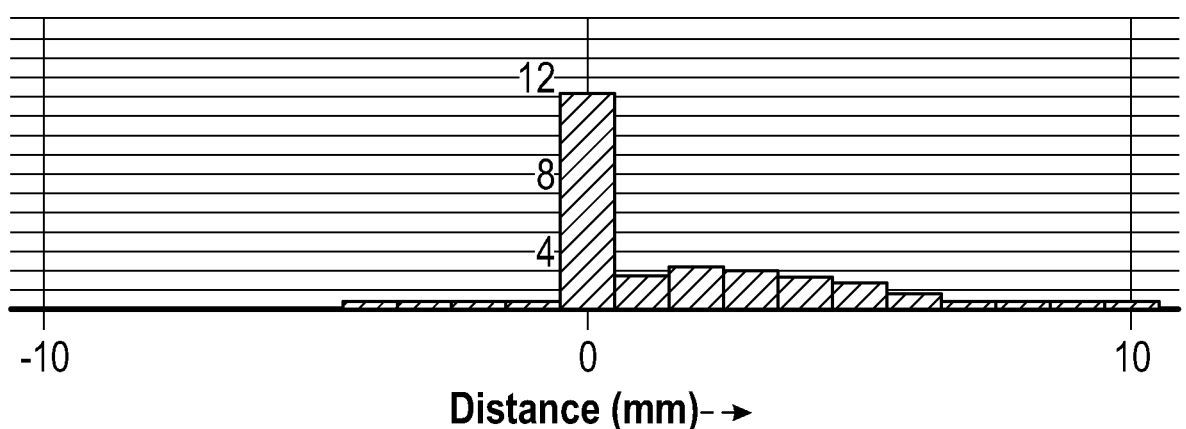
FIGS. 5A-5D depict examples of graphs comparing the two image datasets depicted in FIGS. 4A-4B.

FIG. 5A depicts error versus distance between Set 1 and Set 2. The y-axis represents the error in cubic centimeters (cc) and the x-axis represents distance in millimeters (mm). The anatomy comparison engine, such as the anatomy comparison engines 310, 316 of FIG. 3, determined that the structure of Set 2 is significantly larger than the structure of Set 1.

Figure 5B:
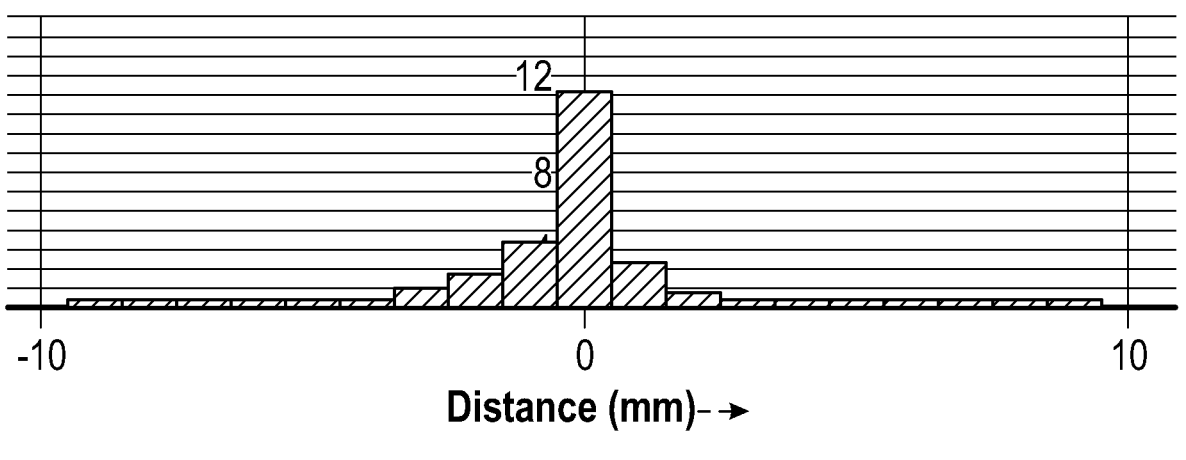

FIG. 5B depicts Vector X versus distance between Set 1 and Set 2. The y-axis represents Vector X in cubic centimeters (cc) and the x-axis represents distance in millimeters (mm). The anatomy comparison engine, such as anatomy comparison engines 310, 316 of FIG. 3, determined that Set 2 has systematic minor shifts in the −X direction (right) compared to Set 1.

Figure 5C:
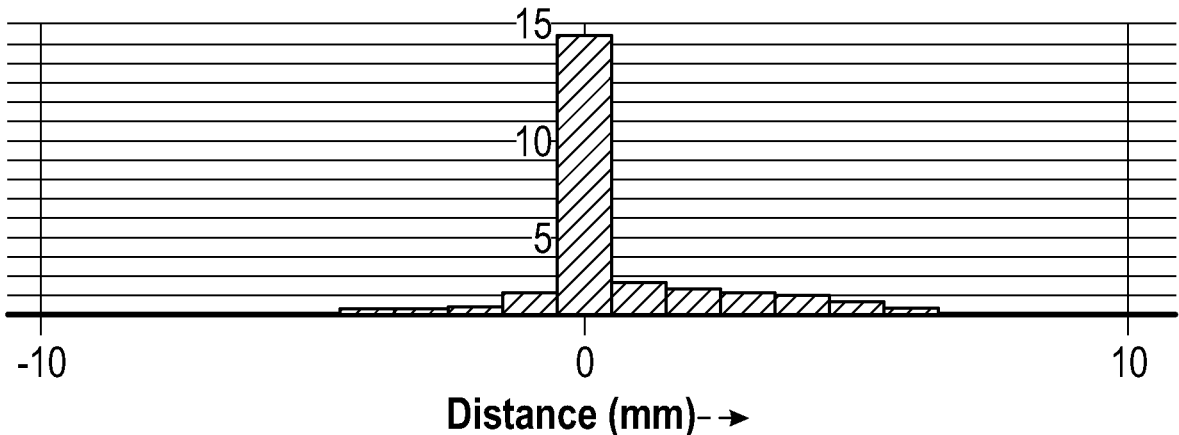

FIG. 5C depicts Vector Y versus distance between Set 1 and Set 2. The y-axis represents Vector Y in cubic centimeters (cc) and the x-axis represents distance in millimeters (mm). The anatomy comparison engine, such as anatomy comparison engines 310, 316 of FIG. 3, determined that Set 2 has systematic major shifts in the +Y direction (superior) compared to Set 1.

Figure 5D:
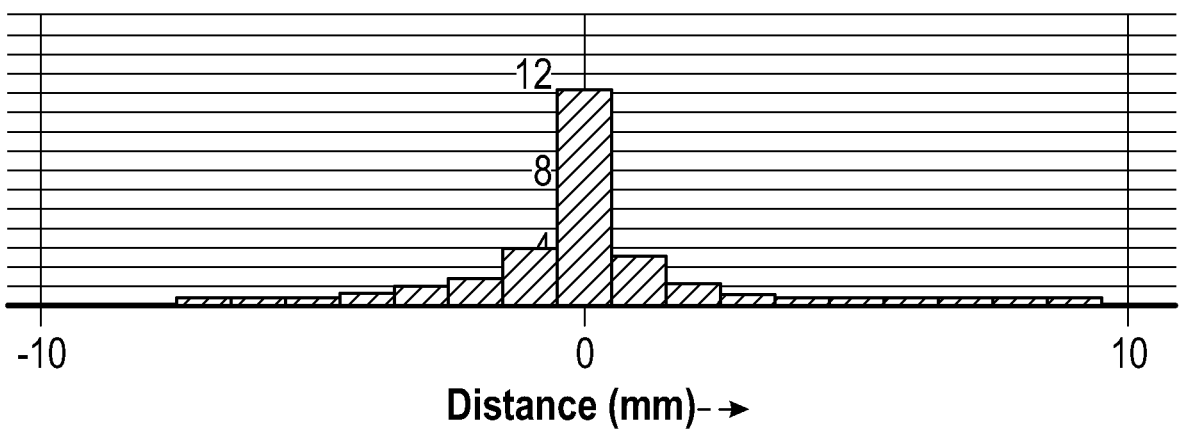

FIG. 5D depicts Vector Z versus distance between Set 1 and Set 2. The y-axis represents Vector Z in cubic centimeters (cc) and the x-axis represents distance in millimeters (mm). The anatomy comparison engine, such as anatomy comparison engines 310, 316 of FIG. 3, determined that Set 2 has systematic minor shifts in the −Z direction (posterior) compared to Set 1.

A non-limiting list of example of measurements used by the anatomy comparison engine are shown below in Table 1.

TABLE 1

| | |
|---|---|
| ROI 1 Volume (cc) | 11.560 |
| ROI 2 Volume (cc) | 21.807 |
| Matching Volume (cc) | 11.183 |
| Extra Volume (cc) | 10.624 |
| Missing Volume (cc) | 0.377 |
| Dice Coefficient | 0.670 |
| Mean Diff Vector Length (mm) | 3.008 |
| Mean Diff Vector X (mm) | −0.393 |
| Mean Diff Vector Y (mm) | 1.199 |
| Mean Diff Vector Z (mm) | −0.327 |

A non-limiting hypothetical is described below for the purposes of illustration. Cancer Center XYZ has two radiation oncologists, Dr. A and Dr. C. The clinical staff wants to know if there are differences in the way the two physicians contour critical anatomy for lung cancer cases.

Dr. A collects the data (images and anatomy contours) for all the lung cancer patients she has treated in the last year (N1=21). Dr. C collects the data (images and anatomy contours) for all the lung cancer patients she has treated in the last year (N2=45).

For the trachea, Dr. A tends to contour 32% larger than the autosegmentation engine in terms of total volume, with major systematic shifts in the +Y (superior) and +Z (anterior) directions. For the trachea, Dr. C tends to contour 5% smaller than the autosegmentation engine in terms of total volume, with a minor systematic shift in the +X (patient's left) direction.

Using a computer-implemented transitive engine, as described above, Dr. A tends to draw 37% larger than Dr. C for the trachea. In addition, for the trachea, Dr. A has major systematic shifts in the +Y (superior) and +Z (anterior) directions compared to Dr. C, and a minor systematic shift in the −X (patient's right) direction.

In this manner, various techniques of this disclosure can provide meaningful feedback for each anatomical structure, organ, lesion, injury, among other things, can be generated based on the comparisons, such as systematic differences in size/volume, left/right dimension, anterior/posterior dimension, and/or superior/inferior dimension.

The techniques described above can be implemented using the machine 400 described below and shown in FIG. 6.

FIG. 6 illustrates a block diagram of an example of a machine upon which any one or more of the techniques (e.g., methodologies) discussed herein can perform. In alternative embodiments, the machine 400 can operate as a standalone device or are connected (e.g., networked) to other machines. In a networked deployment, the machine 400 can operate in the capacity of a server machine, a client machine, or both in server-client network environments. In an example, the machine 400 can act as a peer machine in peer-to-peer (P2P) (or other distributed) network environment. The machine 400 is a personal computer (PC), a tablet PC, a set-top box (STB), a personal digital assistant (PDA), a mobile telephone, a smart phone, a web appliance, a network router, switch or bridge, a server computer, a database, conference room equipment, or any machine capable of executing instructions (sequential or otherwise) that specify actions to be taken by that machine. In various embodiments, machine 400 can perform one or more of the processes described above. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, can include, or can operate on, logic or a number of components, modules, or mechanisms (all referred to hereinafter as "modules"). Modules are tangible entities (e.g., hardware) capable of performing specified operations and is configured or arranged in a certain manner. In an example, circuits are arranged (e.g., internally or with respect to external entities such as other circuits) in a specified manner as a module. In an example, the whole or part of one or more computer systems (e.g., a standalone, client or server computer system) or one or more hardware processors are configured by firmware or software (e.g., instructions, an application portion, or an application) as a module that operates to perform specified operations. In an example, the software can reside on a non-transitory computer readable storage medium or other machine readable medium. In an example, the software, when executed by the underlying hardware of the module, causes the hardware to perform the specified operations.

Accordingly, the term "module" is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software, the general-purpose hardware processor is configured as respective different modules at different times. Software can accordingly configure a hardware processor, for example, to constitute a particular module at one instance of time and to constitute a different module at a different instance of time.

Machine (e.g., computer system) 400 can include a hardware processor 402 (e.g., a central processing unit (CPU), a graphics processing unit (GPU), a hardware processor core, or any combination thereof), a main memory 404, and a static memory 406, some or all of which can communicate with each other via an interlink 408 (e.g., bus). The machine 400 can further include a display unit 410, an alphanumeric input device 412 (e.g., a keyboard), and a user interface (UI) navigation device 414 (e.g., a mouse). In an example, the display unit 410, input device 412 and UI navigation device 414 are a touch screen display. The machine 400 can additionally include a storage device (e.g., drive unit) 416, a signal generation device 418 (e.g., a speaker), a network interface device 420, and one or more sensors 421, such as a global positioning system (GPS) sensor, compass, accelerometer, or other sensor. The machine 400 can include an output controller 428, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 416 can include a machine readable medium 422 on which is stored one or more sets of data structures or instructions 424 (e.g., software) embodying or utilized by any one or more of the techniques or functions described herein. The instructions 424 can also reside, completely or at least partially, within the main memory 404, within static memory 406, or within the hardware processor 402 during execution thereof by the machine 400. In an example, one or any combination of the hardware processor 402, the main memory 404, the static memory 406, or the storage device 416 can constitute machine readable media.

While the machine readable medium 422 is illustrated as a single medium, the term "machine readable medium" can include a single medium or multiple media (e.g., a centralized or distributed database, and/or associated caches and servers) configured to store the one or more instructions 424.

The term "machine readable medium" can include any medium that is capable of storing, encoding, or carrying instructions for execution by the machine 400 and that cause the machine 400 to perform any one or more of the techniques of the present disclosure, or that is capable of storing, encoding or carrying data structures used by or associated with such instructions. Non-limiting machine readable medium examples can include solid-state memories, and optical and magnetic media. Specific examples of machine readable media can include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; Random Access Memory (RAM); Solid State Drives (SSD); and CD-ROM and DVD-ROM disks. In some examples, machine readable media can include non-transitory machine readable media. In some examples, machine readable media can include machine readable media that is not a transitory propagating signal.

The instructions 424 can further be transmitted or received over a communications network 426 using a transmission medium via the network interface device 420. The machine 400 can communicate with one or more other machines utilizing any one of a number of transfer protocols (e.g., frame relay, internet protocol (IP), transmission control protocol (TCP), user datagram protocol (UDP), hypertext transfer protocol (HTTP), etc.). Example communication networks can include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, a Long Term Evolution (LTE) family of standards, a Universal Mobile Telecommunications System (UMTS) family of standards, peer-to-peer (P2P) networks, among others. In an example, the network interface device 420 can include one or more physical jacks (e.g., Ethernet, coaxial, or phone jacks) or one or more antennas to connect to the communications network 426. In an example, the network interface device 420 can include a plurality of antennas to wirelessly communicate using at least one of single-input multiple-output (SIMO), multiple-input multiple-output (MIMO), or multiple-input single-output (MISO) techniques. In some examples, the network interface device 420 can wirelessly communicate using Multiple User MIMO techniques.

Examples, as described herein, can include, or can operate on, logic or a number of components, modules, or mechanisms. Modules are tangible entities (e.g., hardware) capable of performing specified operations and are configured or arranged in a certain manner. In an example, circuits are arranged (e.g., internally or with respect to external entities such as other circuits) in a specified manner as a module. In an example, the whole or part of one or more computer systems (e.g., a standalone, client, or server computer system) or one or more hardware processors are configured by firmware or software (e.g., instructions, an application portion, or an application) as a module that operates to perform specified operations. In an example, the software can reside on a machine-readable medium. In an example, the software, when executed by the underlying hardware of the module, causes the hardware to perform the specified operations.

Accordingly, the term "module" is understood to encompass a tangible entity, be that an entity that is physically constructed, specifically configured (e.g., hardwired), or temporarily (e.g., transitorily) configured (e.g., programmed) to operate in a specified manner or to perform part or all of any operation described herein. Considering examples in which modules are temporarily configured, each of the modules need not be instantiated at any one moment in time. For example, where the modules comprise a general-purpose hardware processor configured using software, the general-purpose hardware processor is configured as respective different modules at different times. Software can accordingly configure a hardware processor, for example, to constitute a particular module at one instance of time and to constitute a different module at a different instance of time.

Various embodiments are implemented fully or partially in software and/or firmware. This software and/or firmware can take the form of instructions contained in or on a non-transitory computer-readable storage medium. Those instructions can then be read and executed by one or more processors to enable performance of the operations described herein. The instructions are in any suitable form, such as but not limited to source code, compiled code, interpreted code, executable code, static code, dynamic code, and the like. Such a computer-readable medium can include any tangible non-transitory medium for storing information in a form readable by one or more computers, such as but not limited to read only memory (ROM); random access memory (RAM); magnetic disk storage media; optical storage media; flash memory; etc.

Figure 7:
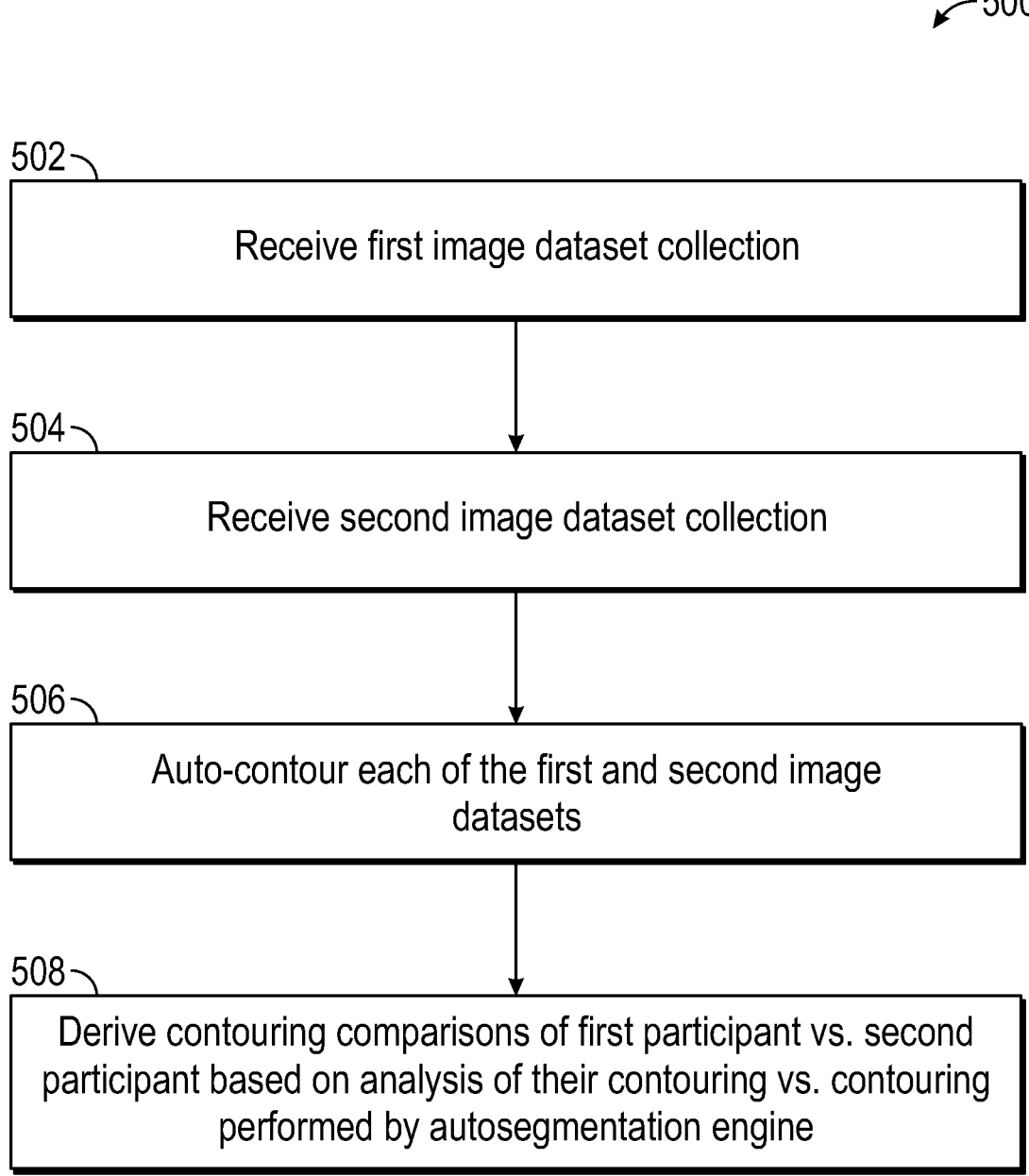
FIG. 7 is a flow diagram illustrating an example of a computer-implemented method of comparing image contouring by different human participants without requiring that the different participants contour a shared image dataset.

FIG. 7 is a flow diagram illustrating an example of a computer-implemented method 500 of comparing image contouring by different human participants without requiring that the different participants contour a shared image dataset. At block 502, the method can include receiving a first image dataset collection, including one or more first image datasets of one or more human or animal subjects produced by an imaging modality, and including first contouring data generated by a first participant. For example, a computer-implemented autosegmentation engine, such as the computer-implemented autosegmentation engine 304 of FIG. 3, can receive the first image dataset collection 300, including one or more first image datasets of one or more human or animal subjects produced by an imaging modality, and including first contouring data generated by the first participant A.

At block 504, the method can include receiving a second image dataset collection, including one or more second image datasets of one or more human or animal subjects produced by the imaging modality, including second contouring data generated by a second participant. For example, a computer-implemented autosegmentation engine, such as the computer-implemented autosegmentation engine 304 of FIG. 3, can receive the second image dataset collection 302, including one or more second image datasets of one or more human or animal subjects produced by the imaging modality, including second contouring data generated by the second participant B.

At block 506, the method can include auto-contouring each of the first and second image datasets, using a computer-implemented autosegmentation engine to obtain third contouring data generated by the autosegmentation engine without requiring human contouring and without requiring identical or overlapping first and second image datasets. For example, without requiring human contouring and without requiring identical or overlapping first and second image datasets, the computer-implemented autosegmentation engine 304 can auto-contour each of the first and second image datasets received from participants A and B, to obtain third contouring data generated by the autosegmentation engine.

At block 508, the method can include comparing contouring by the first participant to contouring by the second participant, including comparing the first contouring data generated by the first participant to the third contouring data generated by the autosegmentation engine to generate first comparison data, and also comparing the second contouring data generated by the second participant to the third contouring data generated by the autosegmentation engine to generate second comparison data. In other words, the method can derive contouring comparisons of the first participant versus the second participant based on an analysis of their contouring versus the contouring performed by the autosegmentation engine, such as the autosegmentation engine 304 of FIG. 3. As described above, the techniques of this disclosure do not directly compare the first participant (A) and the second participant (C) for the same datasets, but first participant (A) and the second participant (C) for different datasets based on analytics of first participant (A) versus B and the second participant (C) versus the computer-implemented autosegmentation engine "B", such as the computer-implemented autosegmentation engine 304 of FIG. 3.

For example, a computer-implemented first anatomy comparison engine, such as the anatomy comparison engine 310 of FIG. 3, can compare the first contouring data generated by the first participant A to the third contouring data generated by the autosegmentation engine 304 to generate first comparison data 315. Similarly, a computer-implemented second anatomy comparison engine, such as the anatomy comparison engine 316 of FIG. 3, can compare the second contouring data generated by the second participant C to the third contouring data generated by the autosegmentation engine to generate second comparison data 322.

Then, a computer-implemented transitive engine, such as the computer-implemented transitive engine 324 of FIG. 3, can, using a transitive property, compare contouring by the first participant A to contouring by the second participant B. For example, the computer-implemented transitive engine 324 can compare the first comparison data 315 and the second comparison data 322 to determine statistically significant trends in systematic differences in size/volume, left/right dimension, anterior/posterior dimension, and/or superior/inferior dimension between the first participant A and the second participant B.

Figure 8:
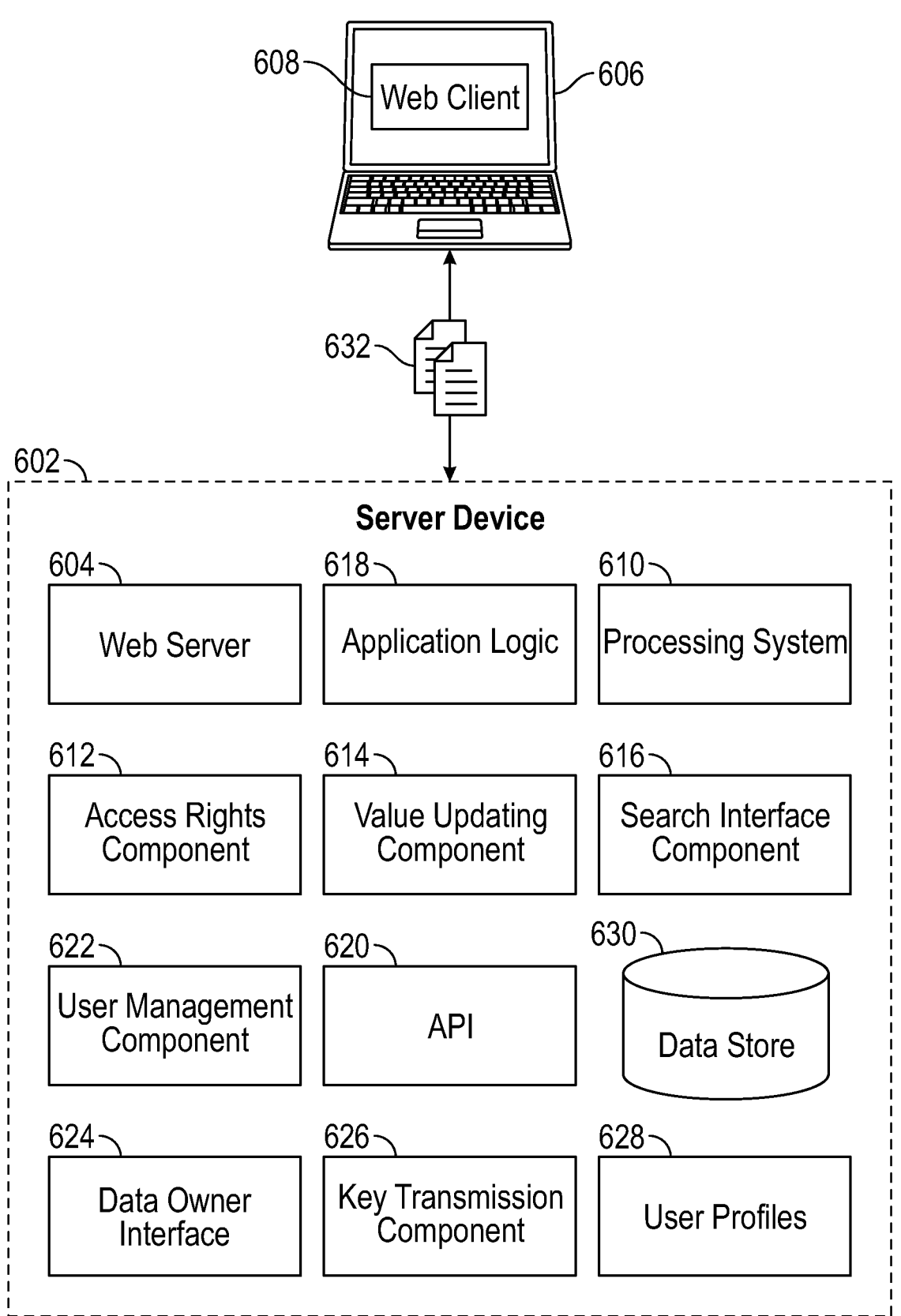
FIG. 8 is an illustration of components of a client device and server device according to various examples.

In some implementations, the operations described above for implementing the autosegmentation techniques, e.g., storage, access, computations, etc., can be implemented using a single computing device (e.g., a server, FPGA, ASIC, SOC, a virtual server, etc.). In other implementations, at least some of the operations described above for implementing the autosegmentation techniques, e.g., storage, access, computations, etc., can be distributed across multiple computing devices (e.g., a server cluster, a cloud computing platform, a virtual server cluster, etc.), such as being implemented in the "cloud" using a computer server device (or "server"). FIG. 8 describes various components that can be used to implement the techniques using a computer server device.

For example, comparing contouring by the first participant to contouring by the second participant, can be performed by a computer server device, such as the server device 602, such as located in a cloud computing platform. The computer server device can compare the first contouring data generated by the first participant to the third contouring data generated by the autosegmentation engine to generate first comparison data, and also compare the second contouring data generated by the second participant to the third contouring data generated by the autosegmentation engine to generate second comparison data.

As another example, the computer server device can generate an indication of one or more differences between contouring by the first and second participants, and transmit the indication to another computing device, such as client device 606 of FIG. 8, or another computer server device.

In some example, the first image dataset collection can be received by the computer server device, and the second image dataset collection can be received by the computer server device.

As described above, the techniques of this disclosure can determine a first quality metric based on the one or more differences between contouring by the first and second participants and provide the first quality metric to the at least one of the first hospital affiliation, the first physician practice group affiliation, or the first geographic location, and can determine a second quality metric based on the one or more differences between contouring by the first and second participants and provide the second quality metric to the at least one of the second hospital affiliation, the second physician practice group affiliation, or the second geographic location. In some examples, the computer server device can determine the first quality metric and the second quality metric.

In some examples, the computer server device can determine a quality metric based on one or more differences between contouring by the first and second participants and provide the quality metric to the at least one of the first hospital affiliation, the first physician practice group affiliation, or the first geographic location.

In some examples, the computer server device, such as the computer server device 602 of FIG. 8, can automatically anonymize the image datasets, such as after the image datasets are uploaded to the computer server device.

In some examples, the computer server device can transmit information to and receive information from another computing device, such as a client device, such as the client device 606 of FIG. 8.

FIG. 8 is an illustration of components of a client device and server device according to various examples. FIG. 8 includes a server device 602, web server 604, client device 606, web client 608, processing system 610, access rights component 612, value updating component 614, search interface component 616, application logic 618, application programming interface (API) 620, user management component 622, data owner interface 624, key transmission component 626, data store 630, and data 632.

Client device 606 can be a computing device which can be, but is not limited to, a smartphone, tablet, laptop, multi-processor system, microprocessor-based or programmable consumer electronics, game console, set-top box, or other device that a user utilizes to communicate over a network. In various examples, a computing device includes a display module (not shown) to display information (e.g., in the form of specially configured user interfaces). In some embodiments, computing devices can comprise one or more of a touch screen, camera, keyboard, microphone, or Global Positioning System (GPS) device. Client device 606 can be associated with one or more entities that interact with server device 602. An entity can be an individual, group of individuals, or company in various examples.

Client device 606 and Server device 602 can communicate via a network (not shown). The network can include local-area networks (LAN), wide-area networks (WAN), wireless networks (e.g., 802.11 or cellular network), the Public Switched Telephone Network (PSTN) Network, ad hoc networks, cellular, personal area networks or peer-to-peer (e.g., Bluetooth®, Wi-Fi Direct), or other combinations or permutations of network protocols and network types. The network can include a single Local Area Network (LAN) or Wide-Area Network (WAN), or combinations of LAN's or WAN's, such as the Internet.

Client device 606 and server device 602 can communicate data 632 over the network. Data 632 can be, but is not limited to, search requests, search results, data item (as discussed in more detail below) requests, data items, decryptions keys, and data inheritance details.

In some examples, the communication can occur using an application programming interface (API) such as API 620. An API provides a method for computing processes to exchange data. A web-based API (e.g., API 620) can permit communications between two or more computing devices such as a client and a server. The API can define a set of HTTP calls according to Representational State Transfer (RESTful) practices. For examples, A RESTful API can define various GET, PUT, POST, DELETE methods to create, replace, update, and delete data stored in a database (e.g., data store 630).

APIs can also be defined in frameworks provided by an operating system (OS) to access data in an application that an application can not regularly be permitted to access. For example, the OS can define an API call to obtain the current location of a mobile device the OS is installed on. In another example, an application provider can use an API call to request a user be authenticated using a biometric sensor on the mobile device. This can allow the user to access information stored in a data item. By segregating any underlying biometric data—e.g., by using a secure element—the risk of unauthorized transmission of the biometric data can be lowered.

Server device 602 is illustrated as set of separate elements (e.g., component, logic, etc.). However, the functionality of individual elements can be performed by a single element. An element can represent computer program code that is executable by processing system 610. The program code can be stored on a storage device (e.g., data store 630) and loaded into a memory of the processing system 610 for execution. Portions of the program code can be executed in a parallel across multiple processing units (e.g., a core of a general-purpose computer processor, a graphical processing unit, an application specific integrated circuit, etc.) of processing system 610. Execution of the code can be performed on a single device or distributed across multiple devices. In some example, the program code can be executed on a cloud platform (e.g., MICROSOFT AZURE® and AMAZON EC2®) using shared computing infrastructure.

Server device 602 can include web server 604 to enable data exchanges with client device 606 via web client 608. Although generally discussed in the context of delivering webpages via the Hypertext Transfer Protocol (HTTP), other network protocols can be utilized by web server 604 (e.g., File Transfer Protocol, Telnet, Secure Shell, etc.) A user can enter in a uniform resource identifier (URI) into web client 608 (e.g., the INTERNET EXPLORER® web browser by Microsoft Corporation or SAFARI® web browser by Apple Inc.) that corresponds to the logical location (e.g., an Internet Protocol address) of web server 604. In response, web server 604 can transmit a web page that is rendered on a display device of a client device (e.g., a mobile phone, desktop computer, etc.).

Additionally, web server 604 can enable a user to interact with one or more web applications provided in a transmitted web page. A web application can provide user interface (UI) components that are rendered on a display device of client device 606. The user can interact (e.g., select, move, enter text into) with the UI components, and based on the interaction, the web application can update one or more portions of the web page. A web application can be executed in whole, or in part, locally on client device 606. The web application can populate the UI components with data from external sources or internal sources (e.g., data store 630) in various examples.

For example, server device 602 can provide a web application (e.g., search interface component 616) to a user to search the metadata of a data store of data items (e.g., data store 630). For example, an input box can be presented that receives text entered by a user. The text can be formatted as a database query (e.g., SQL) and issued to a database to retrieve data items that have data in fields that match the text entered by the user. A web application (e.g., data owner interface 624 and access rights component 612) can also provide user interfaces for owner users to edit access rights, etc., of their data items. For example, user interface elements can be presented to add or revoke access rights to a data item's payload.

The interface can also allow a user to group data items based on features in the metadata (e.g., type, data source, etc.). For example, the user can submit a search query to retrieve all data items that correspond to user preferences on movies. The interface can include an option to select one or more of the results and create a group of the selected results. Data store 630 can store an indication that the selected data items are part of the same group in various examples. The web application can also allow editing access rights of a group instead of requiring the user to individually edit each data item.

The web application can be executed according to application logic 618. Application logic 618 can use the various elements of server device 602 to implement the web application. For example, application logic 618 can issue API calls to retrieve or store data from data store 630 and transmit it for display on client device 606. Similarly, data entered by a user into a UI component can be transmitted using API 620 back to the web server 604. Application logic 618 can use other elements (e.g., access rights component 612, value updating component 614, search interface component 616, application logic 618, etc.) of server device 602 to perform functionality associated with the web application as described further herein.

Data store 630 can store data that is used by server device 602 (e.g., user profiles 628, data items, decryption keys, etc.). Data store 630 is depicted as singular element but can in actuality be multiple data stores. The specific storage layout and model used in by data store 630 can take a number of forms—indeed, a data store 630 can utilize multiple models. Data store 630 can be, but is not limited to, a relational database (e.g., SQL), non-relational database (NoSQL) a flat file database, object model, document details model, graph database, shared ledger (e.g., blockchain), or a file system hierarchy. Data store 630 can store data on one or more storage devices (e.g., a hard disk, random access memory (RAM), etc.). The storage devices can be in stand-alone arrays, part of one or more servers, and can be located in one or more geographic areas.

User profiles 628 can store the profiles of users that interact with server device 602. A user profile can include a user identifier (e.g., a username) and a password. A user profile can also include a role of the user. A user can have multiple roles. Roles can include an owner role, a buyer role (e.g., those looking to purchase access to data items), a data aggregator role (e.g., data item providers), among others. When a user logs into server device 602 (e.g., via web server 604) functionality related to the roles of the user can be provided. For example, in a buyer role, server device 602 can present a search interface to find data items for purchase. In an owner role, server device 602 can present a user interface to edit the access rights of the user's data items.

Value updating component 614 can generate or update values of data items. A data item can have an initial value determined in a number of ways. For example, an owner user can enter in some value (e.g., a quantitative value such as $0.50 or qualitative value such as high, medium, etc.) for their data items. If the owner does not enter in a value, server device 602 can assign the data item a value based on its metadata. For example, a weighted calculation can be made that uses when the data item was generated (recent data is given a higher value, etc.), the type of data (e.g., location data has one default value, user preference has a default value), etc. In some examples, the calculated value can be presented to the owner for confirmation before being stored as part of the data item.

Periodically, value updating component 614 can iterate through one or more data items stored in data store 630 and update the values of the data item. For example, a formula—e.g., similar or identical to the weighted calculation above—can be stored that calculates a value for the data item based on the metadata of the data item. In other examples, an adjustment calculation can be used that decreases or increases the value based on a change in one or more of the metadata fields or a change in a subject user of the data item.

For example, consider that the data item indicates the preferences of a subject user (e.g., the user to which the data payload pertains) to go to a particular coffee shop in a specific zip code. Now, consider that the subject user no long lives near that zip code. The change in location information can be based on server device 602 receiving location information from a computing device of the subject user—assuming the subject user grants such location access. Thus, if the current location of the subject user is within an X miles radius from the zip code and/or has not been within that radius within the past month, the data item can become less valuable. Accordingly, value updating component 614 can lower the value of the data item by a certain amount or percentage amount.

In another example, server device 602 can receive information (e.g., via API 620) that the subject user is incapacitated or deceased. In such a scenario, value updating component 614 can set the value of all data items associated with the subject user to 0 (or some other nominally low value).

Access rights component 612 can be configured to update a data item and/or data store 630 to indicate which users have access to the data item. For example, a data item can include a token and the token include a list of identifiers corresponding to the users that have access to the data item. Access rights component 612 can update the token to include or remove user identifications. An identification can be added based on a user purchasing access to the data item. If a user has been granted access to a data item, key transmission component 626 can transmit a decryption key for the data payload to the purchasing user. In various examples, access to a data item is limited. For example, a data item can only be accessed for a certain duration of time. Thus, once the time period has lapsed, the token can be updated to remove access.

In some examples, it can be desirable to present a user interface to a user, such as physician, clinician, or other health provider personnel, that displays data representing any missing, common, and/or extra volume in a comparison between the first contouring, generated by the first participant, and the second contouring, generated by the second participant. Examples of user interfaces are shown in FIGS. 9 and 10.

Figure 9:
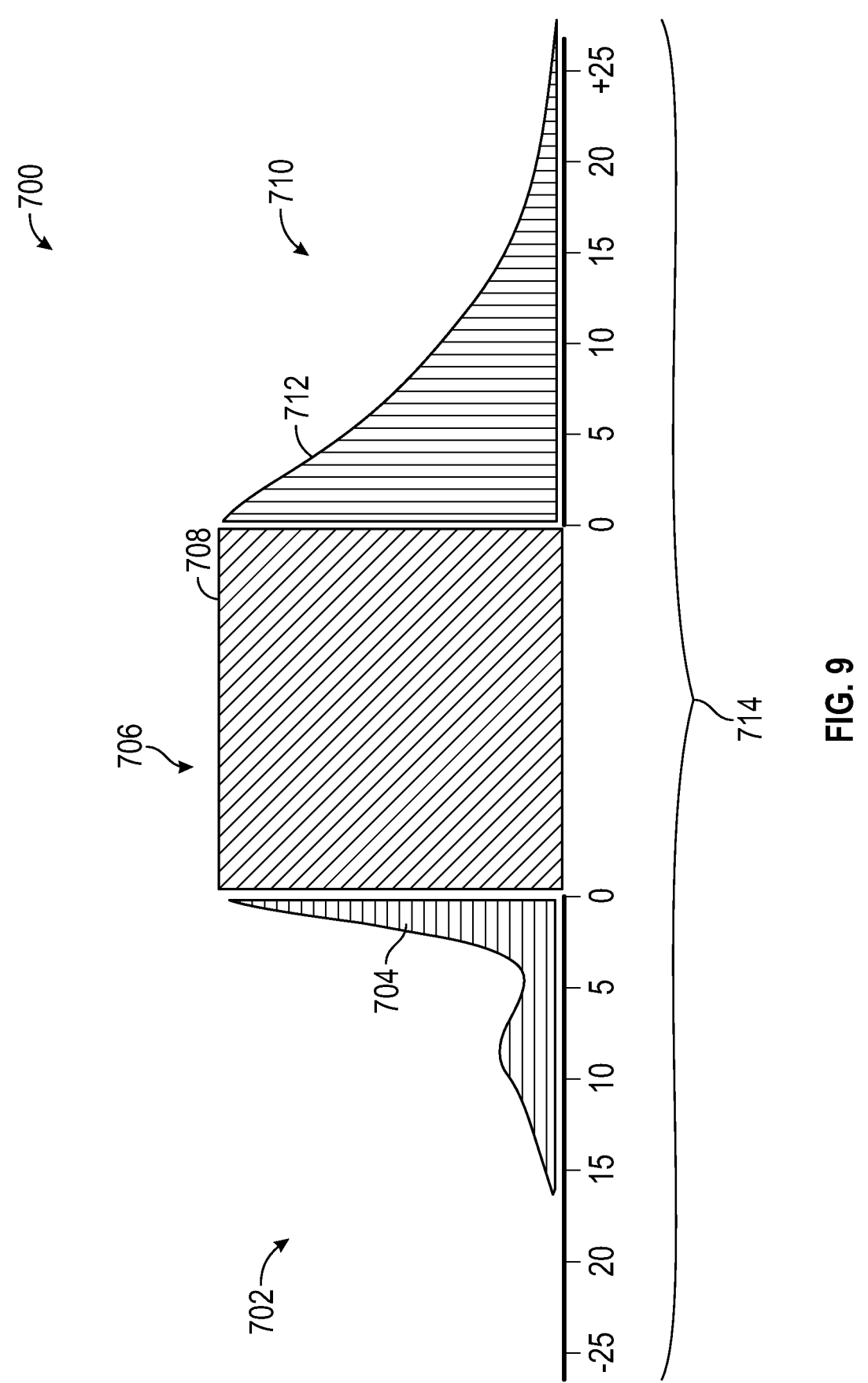
FIG. 9 is an example of a user interface associated with computer-implemented method of comparing image contouring by different human participants without requiring that the different participants contour a shared image dataset.

FIG. 9 is an example of a user interface associated with computer-implemented method of comparing image contouring by different human participants without requiring that the different participants contour a shared image dataset.

As mentioned above, an anatomy comparison engine can perform voxelization of contoured anatomy into sufficiently high-resolution volume elements (e.g., 0.001 cc, or 1 mm per side) and analysis of all matching (common), missing, and extra voxels in the first set versus the second set. Matching (or common) voxels are those voxels that are shared by both the first contouring, generated by the first participant (such as healthcare provider participant A), and the second contouring, generated by the second participant (such as healthcare provider participant B). Missing voxels are those voxels that are not present in the first contouring but present in the second contouring (missing from the point of view of participant A). Extra voxels are those voxels that are present in the first contouring but not present in the second contouring (extra from the point of view of participant A).

The anatomy comparison engines 310, 316 of FIG. 3 can perform a per voxel determination of difference vectors that are 3D "vector-to-agreement" lines connecting un-matched (missing or extra) voxels to the closest point on the surface of the other volume.

In some examples, a difference distance is the total length of a difference vector. Matching voxels can have 0 mm difference, missing voxels can have a negative difference distance based on how far away they are from the other set's surface, and extra voxels can have a positive difference distance.

The comparison can yield, for each anatomic volume in each dataset, the following: 1) comparisons of absolute volume (e.g., size); 2) distribution of missing, matching, and extra volume for set 1 vs. set 2 as a histogram of contoured volume versus difference distance; 3) histogram of the x-component (usually patient L-R) of the difference vectors, as well as mean and standard deviation of the differences in that dimension; 4) histogram of the y-component (usually patient superior-inferior) of the difference vectors, as well as mean and standard deviation of the differences in that dimension; and/or 5) histogram of the z-component (usually patient anterior-posterior) of the difference vectors, as well as mean and standard deviation of the differences in that dimension.

The user interface 700 shown in FIG. 9 is an example of a user interface that can be presented, such as transmitted for display or displayed by a video display, such as by the video display 410 of FIG. 6, to a physician, clinician, healthcare provider personnel, or other user. The user interface 700 can include a first portion 702 that is configured to display data of a first representation 704 of a volume that is not present in a first contouring, generated by a first participant, of a target or an organ at risk of a first group of subjects but present in a second contouring, generated by a second participant, of a target or an organ at risk of a second group of subjects. In some examples, the first group of subjects can include at least some subjects that are not included in the second group of subjects. In other examples, the subjects in the first group of subjects can be completely different from the subjects in the second group of subjects. In some examples, the subjects in the first group of subjects can be the same subjects as those in the second group of subjects.

In some examples, the first group of subjects can include 10 or more subjects, such as 20 or more subjects, such as 100 subjects. Similarly, the second group of subjects can include 10 or more subjects, such as 20 or more subject, such as 100 subjects. In some examples, the target or the organ at risk of the first subject and the target or the organ at risk of the second subject can be similar targets or organs at risk, e.g., liver, lung, prostate, etc.

The data of the first representation 704 of a volume can represent the "missing" voxels, which represent a volume (e.g., cubic centimeters), determined by the anatomy comparison engines 310, 316 of FIG. 3 and the transitive engine 324 of FIG. 3, aggregated over multiple subjects, such as 10, 20, 100, or more subjects, to provide statistically meaningful trends with respect to how participant A contours targets or organs at risk of subjects as compared with how participant B contours targets or organs at risk of subjects over a sample size. The distribution of errors is captured by the x-axis, which shows the distance error of "missing" volume. The user interface 700 can include a fourth portion 714 configured to display data representing a distribution of errors between the first contouring and the second contouring.

The user interface 700 can include a second portion 706 that is configured to display data of a second representation 708 of a volume, which represent a volume (e.g., cubic centimeters), that is shared by both the first contouring and the second contouring. The data of the second representation 708 of a volume can represent the "extra" voxels determined by the anatomy comparison engines 310, 316 of FIG. 3 and the transitive engine 324 of FIG. 3, aggregated over multiple subjects, such as 10, 20, 100 subjects, to provide a statistically meaningful trend with respect to how participant A contours as compared with how participant B contours over a sample size.

The user interface 700 can include a third portion 710 that is configured to display data of a third representation 712 of a volume, which represent a volume (e.g., cubic centimeters), that is present in the first contouring but not present in the second contouring. The data of the third representation 712 of a volume can represent the "extra" voxels determined by the anatomy comparison engines 310, 316 of FIG. 3 and the transitive engine 324 of FIG. 3, aggregated over multiple subjects, such as 10, 20, 100 subjects, to provide a statistically meaningful trend with respect to how participant A contours as compared with how participant B contours over a sample size. The distribution of errors is captured by the x-axis, which shows the distance error of "extra" volume.

In FIG. 9, the portions 702, 706, and 710 of the user interface 700 are not displaying anatomical images. Instead, the user interface 700 graphically presents trends in differences, such as systematic differences, in contouring performed by two different participants, such as over a statistically meaningful size of subjects, such 10 or more subjects. That is, the user interface 700 can present a rendering of systematic differences between the contouring performed by two participants. The systematic differences shown can represent an extent, a direction, and an identification, such as "extra", "missing", "common", by how much, in what direction. A processor, such as the processor 402 of FIG. 6, can determine directions of differences and the location of the differences in volumetric regions or sub-regions, perform a summation, and then perform an averaging. By way of example, some of the "extra" volume was in the bin between 19.5 mm and 20.5 mm.

In some examples, the first representation 704, the second representation 706, and the third representation 712 are visually distinguishable from each other, such as different colors or grayscale shapes.

In some examples, to get insights into directional or sub-regions of an entire volume, a user can select a volumetric sub-region and show the results only for volume elements in that region. Examples include, but are not limited to, the following:

Volumetric Halves: left or right half, superior or inferior half, anterior or posterior half;

Volumetric Quadrants: Left-Anterior quadrant, Right-Anterior quadrant, Left-Posterior quadrant, Right-Posterior quadrant; and Volumetric Eighths: Left-Anterior-Superior, Left-Anterior-Inferior, Left-Posterior-Superior, Left-Posterior-Inferior, Right-Anterior-Superior, Right-Anterior-Inferior, Right-Posterior-Superior, Right-Posterior-Inferior. For any selected volumetric sub-region, the graphic shown in FIG. 9 can be displayed.

In some examples, the graphic shown in FIG. 9 can be a two-dimensional shape. In other examples, the graphic shown in FIG. 9 can be a three-dimensional shape.

Figure 10:
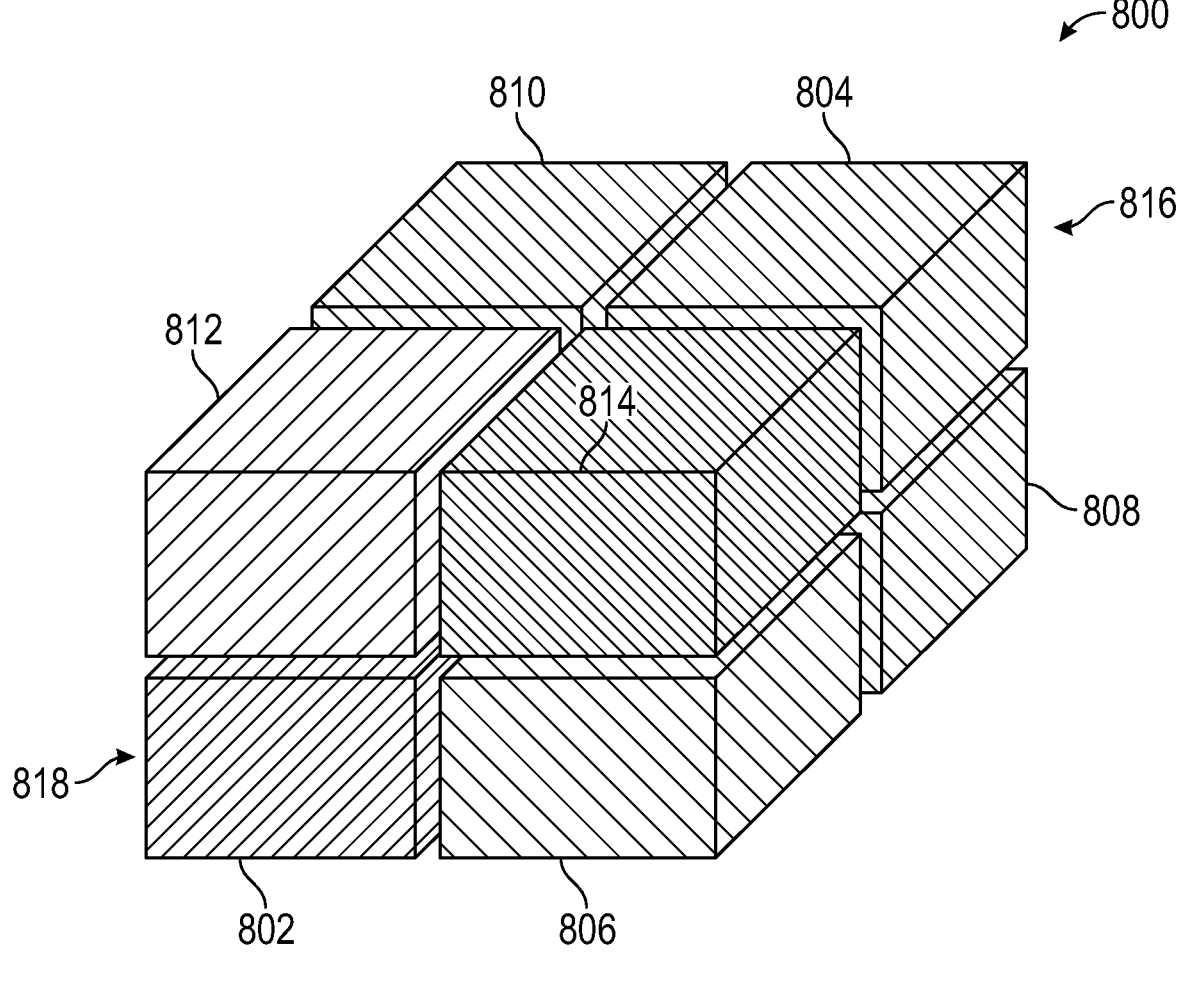
FIG. 10 is another example of a user interface associated with computer-implemented method of comparing image contouring by different human participants without requiring that the different participants contour a shared image dataset.

FIG. 10 is another example of a user interface associated with computer-implemented method of comparing image contouring by different human participants without requiring that the different participants contour a shared image dataset. For any selected volumetric sub-region, the graphic shown in FIG. 10 can be displayed. In some examples, the graphic shown in FIG. 10 can be a three-dimensional shape.

The user interface 800 shown in FIG. 10 is an example of a user interface that can be presented, such as transmitted for display or displayed by a video display, such as by the video display 410 of FIG. 6, to a physician, clinician, healthcare provider personnel, or other user. The user interface 800 can display, for example, trends in selected sub-regions. A number of sub-regions 802-814 are shown in FIG. 10. For example, the region 802 can represent the Right-Posterior-Inferior region (out of 8 regions) and the region 804 can represent the Left-Anterior-Superior region (out of 8 regions). The regions 802-814 can be visually distinguishable from one another, such as using different colors or grayscale shapes.

The user interface 800 can include a first portion, such as portion 816, that is configured to display data of a representation of a volume that is present in a first contouring of a target or an organ at risk of a first group of subjects but not present in a second contouring of a target or an organ at risk of a second group of subjects (the "extra" voxels).

The user interface 800 can include a second portion, such as portion 818, that is configured to display data of another representation of a volume that is not present in the first contouring but present in the second contouring (the "missing" voxels).

As an example, a first color of the region 802, such as blue, can indicate that there is a large portion of "missing" volume in the selected sub-region, when comparing the first participant's contouring to the second participant's contouring. As another example, a second color of the region 804, such as red, can indicate that there is a large portion of "extra" volume in the selected sub-region, when comparing the first participant's contouring to the second participant's contouring.

In this manner, the user interface 800 can show a summary of trends in particular sub-regions. If participant A contours a lot more volume than participant B in a particular sub-region, the user interface 800 can display a first color for that sub-region, and if participant A contours a lot less volume than participant B in a particular sub-region, the user interface 800 can display a second color for that sub-region.

A processor, such as the processor 402 of FIG. 6, can perform statistical calculations for a region, perform further data reduction, and using various colors, for example, to visually distinguish sub-regions, display trends. For example, if the processor determines that an average difference between contouring by participant A and participant B is 3 mm "extra", an associated color, such as red, can be displayed for that particular sub-region.

The shade or intensity of a color, for example, can provide an indication of the relative error in terms of extra or missing volumes. For example, a light blue, such as in the region 812, or a light red, such as in the region 814, can indicate that there is less relative error in those regions than in the regions 802, 804, respectively. As an example, a deep red color can mean that there is a lot more "extra" voxels than "missing" voxels in a particular sub-region, and/or a lot more "extra" voxels at a larger distance. If the amount of "extra" volume in the 2D image in FIG. 9 is equal to the amount of "missing" volume in the 2D image in FIG. 9, then FIG. 10 can display another color, e.g., white, to indicate that there was no trend in the data.

By selecting one of the sub-regions 802-814 shown in FIG. 10, additional information can be shown, such as depicted in FIG. 9. For example, the user interface 700 shown in FIG. 9 can represent the sub-region 804 of FIG. 10.

Various Notes

Each of the non-limiting aspects or examples described herein may stand on its own, or may be combined in various permutations or combinations with one or more of the other examples.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact discs and digital video discs), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

The claimed invention is:

1. A computer-implemented method of comparing image contouring by different human participants without requiring that the different human participants contour a shared image dataset, the method comprising:

receiving a first image dataset collection, including one or more first image datasets of one or more human or animal subjects produced by an imaging modality, and including first contouring data generated by a first human participant on the one or more first image datasets;

receiving a second image dataset collection, including one or more second image datasets of one or more human or animal subjects produced by the imaging modality, including second contouring data generated by a second human participant on the one or more second image datasets, the one or more second image datasets not overlapping with images in the one or more first image datasets;

auto-contouring the first one or more first image datasets and the second one or more image datasets, using a computer-implemented autosegmentation engine to generate participant-specific computational reference contours third contouring data generated by the autosegmentation engine without requiring human contouring and without requiring identical or overlapping first and second image datasets, wherein the computational reference contours for each participant are generated from a participant's respective image datasets;

comparing contouring by the first human participant to contouring by the second human participant by:

comparing the first contouring data generated by the first human participant to the participant-specific computational reference contours of the third contouring data for the first human participant generated by the autosegmentation engine to generate first comparison data:

comparing the second contouring data generated by the second human participant to the participant-specific computational reference contours of the third contouring data for the second human participant generated by the autosegmentation engine to generate second comparison data; and performing a transitive analysis comparison of the first human participant to the second human participant by separately analyzing the first comparison data and the second comparison data relative to a common reference provided by the third contouring data generated by the autosegmentation engine;

generating an indication of one or more systemic differences between contouring by the first and second human participants based on the transitive analysis; and displaying, on a user interface, the indication of the one or more systemic differences, wherein the indication includes visually distinguishable representations of missing, extra, and common volumes.

2. The method of claim 1, wherein the indication of one or more systematic differences includes at least one of:

an indication of a systematic difference in a contoured volume;

an indication of a systematic difference in a lateral contoured dimension;

an indication of a systematic difference in an anterior or posterior contoured dimension; or an indication of a systematic difference in a superior or inferior contoured dimension.

3. The method of claim 2, wherein the contoured volume or dimension includes at least one of:

a contoured organ volume or dimension;

a contoured organ substructure volume or dimension;

a contoured anatomical structure volume or dimension; or an injured or diseased region structure volume or dimension.

4. The method of claim 1, wherein the indication of the one or more systemic differences are normalized with respect to a parameter based upon a contour generated by the autosegmentation engine.

5. The method of claim 1, wherein at least one of the first image dataset collection and the second image dataset collection includes metadata, in addition to the human first contouring data or second contouring data, wherein the metadata is provided as an input to the autosegmentation engine.

6. The method of claim 5, wherein the metadata includes at least one of:

an indication of at least one imaging modality type or other imaging modality parameter used to generate images in a corresponding image dataset;

an indication of a characteristic of an organ or other target structure to be targeted for treatment;

an indication of a characteristic of an organ or other structure at risk to be avoided for treatment;

an indication of a characteristic of a patient demographic of the human or animal subject corresponding to images in a corresponding image dataset;

an indication of a disease characteristic associated with the human or animal subject corresponding to images in a corresponding image dataset;

an indication of a treatment characteristic associated with the human or animal subject corresponding to images in a corresponding image dataset; and an indication of a desired treatment outcome associated with the human or animal subject corresponding to images in a corresponding image dataset.

7. The method of claim 1, wherein the autosegmentation engine is configured to perform the auto-contouring by including or using an atlas-based model.

8. The method of claim 1, wherein the autosegmentation engine is configured to perform the auto-contouring by including or using a trained model, the trained model trained using at least one or more of statistical learning, artificial intelligence, machine learning, neural networks, generative adversarial network, or deep learning.

9. The method of claim 8, wherein the model is trained independently using a different and independent learning image dataset.

10. The method of claim 9, wherein:

the different and independent learning image dataset includes images from a population of human or animal subjects overlapping with at least one the first and second image datasets.

11. The method of claim 1, wherein at least one of the comparing the first contouring data generated by the first human participant to the third contouring data generated by the autosegmentation engine, or the comparing the second contouring data generated by the second human participant to the third contouring data generated by the autosegmentation engine comprises:

voxel analysis of a human-contoured region compared to an auto-contoured region.

12. The method of claim 11, further comprising:

analyzing a distance between (1) one or more unmatched voxels, between the human-contoured region and the auto-contoured region, and (2) a closest voxel location matched between the human-contoured region and the auto-contoured region.

13. The method of claim 12, further comprising:

analyzing a direction between (1) one or more unmatched voxels, between the human-contoured region and the auto-contoured region, and (2) a closest voxel location matched between the human-contoured region and the auto-contoured region.

14. The method of claim 11, further comprising:

generating a statistical representation of difference vectors between (1) one or more unmatched voxels, between the human-contoured region and the auto-contoured region, and (2) a closest voxel location matched between the human-contoured region and the auto-contoured region.

15. The method of claim 1, wherein comparing contouring by the first human participant to contouring by the second human participant comprises comparing contouring by the first human participant to individual or aggregated contouring by a group or population of second human participants.

16. The method of claim 1, wherein comparing contouring by the first human participant to contouring by the second human participant comprises comparing individual or aggregated contouring by a group or population of first human participants to individual or aggregated contouring by a group or population of second human participants.

17. The method of claim 1, further comprising generating a quality metric based on the comparing.

18. The method of claim 1, wherein an individual or aggregated contouring by a group or population of second human participants provides a gold standard benchmark against which the individual or aggregated contouring by the group or population of the first human participants is compared.

19. The method of claim 1, comprising selecting human participants for contouring in a clinical study on human or animal subjects, wherein the selection is based at least in part on a quality metric.

20. The method of claim 1, comprising healthcare provider participants associated with at least one of a hospital affiliation, a physician practice group affiliation, or a geographic location.

21. The method of claim 1, wherein the comparing contouring by the first human participant to contouring by the second human participant is iterated to compare the second human participant to a third human participant, or further iterated to extend to one or more further human participants.

22. The method of claim 1, wherein a quality metric includes contouring information correlated with at least one of treatment plan information, treatment safety information, treatment efficacy information, or treatment outcome information about one or more treatments carried out using the contouring information.

23. The method of claim 22, wherein at least one of treatment safety information, efficacy information, or outcome information includes toxicity information, including at least one of a toxicity indication, a toxicity prediction, or a toxicity risk indication.

24. The method of claim 22, wherein at least one of treatment safety information, efficacy information, or outcome information includes toxicity information localized to an anatomical structure, sub-structure, or region.

25. A computer-implemented method of comparing image contouring by different human participants without requiring that the different human participants contour a shared image dataset, the method comprising:

receiving a first image dataset collection, including one or more first image datasets of one or more human or animal subjects produced by an imaging modality, and including first contouring data generated by a first human participant on the one or more first image datasets;

receiving a second image dataset collection, including one or more second image datasets of one or more human or animal subjects produced by the imaging modality, including second contouring data generated by a second human participant on the one or more second image datasets, the one or more second image datasets not overlapping with images in the one or more first image datasets;

auto-contouring the first one or more first image datasets and the second one or more image datasets, using a computer-implemented autosegmentation engine to generate participant-specific computational reference contours third contouring data generated by the autosegmentation engine without requiring human contouring and without requiring identical or overlapping first and second image datasets, wherein the computational reference contours for each participant are generated from a participant's respective image datasets;

comparing contouring by the first human participant to contouring by the second human participant by:

comparing the first contouring data generated by the first human participant to the participant-specific computational reference contours of the third contouring data for the first human participant generated by the autosegmentation engine to generate first comparison data:

comparing the second contouring data generated by the second human participant to the participant-specific computational reference contours of the third contouring data for the second human participant generated by the autosegmentation engine to generate second comparison data; and performing a transitive analysis comparison of the first human participant to the second human participant by separately analyzing the first comparison data and the second comparison data relative to a common reference provided by the third contouring data generated by the autosegmentation engine;

generating a quality metric based on one or more systemic differences between contouring by the first and second human participants based on the transitive analysis; and displaying, on a user interface, the quality metric of the one or more systemic differences, wherein the quality metric includes visually distinguishable representations of missing, extra, and common volumes.

26. The method of claim 25, wherein the quality metric includes at least one of contouring information correlated with at least one of treatment plan information, treatment safety information, treatment efficacy information, or treatment outcome information about one or more treatments carried out using the contouring information.

27. A computer-readable storage device comprising instructions, that when executed by at least one processor, configure the at least one processor to:

receive a first image dataset collection, including one or more first image datasets of one or more human or animal subjects produced by an imaging modality, and including first contouring data generated by a first human participant on the one or more first image datasets;

receive a second image dataset collection, including one or more second image datasets of one or more human or animal subjects produced by the imaging modality, including second contouring data generated by a second human participant on the one or more second image datasets, the one or more second image datasets not overlapping with images in the one or more first image datasets;

auto-contour the first one or more first image datasets and the second one or more image datasets, using a computer-implemented autosegmentation engine to generate participant-specific computational reference contours third contouring data generated by the autosegmentation engine without requiring human contouring and without requiring identical or overlapping first and second image datasets, wherein the computational reference contours for each participant are generated from a participant's respective image datasets;

compare contouring by the first human participant to contouring by the second human participant by:

comparing the first contouring data generated by the first human participant to the participant-specific computational reference contours of the third contouring data for the first human participant generated by the autosegmentation engine to generate first comparison data:

comparing the second contouring data generated by the second human participant to the participant-specific computational reference contours of the third contouring data for the second human participant generated by the autosegmentation engine to generate second comparison data; and performing a transitive analysis comparison of the first human participant to the second human participant by separately analyze the first comparison data and the second comparison data relative to a common reference provided by the third contouring data generated by the autosegmentation engine;

generate an indication of one or more systemic differences between contouring by the first and second human participants based on the transitive analysis; and display, on a user interface, the indication of the one or more systemic differences, wherein the indication includes visually distinguishable representations of missing, extra, and common volumes.

28. A system for comparing image contouring by different human participants without requiring that the different human participants contour a shared image dataset, the system comprising:

at least one processor; and computer-readable storage device comprising instructions, that when executed by at least one processor, configure the at least one processor to:

receive a first image dataset collection, including one or more first image datasets of one or more human or animal subjects produced by an imaging modality, and including first contouring data generated by a first human participant on the one or more first image datasets;

receive a second image dataset collection, including one or more second image datasets of one or more human or animal subjects produced by the imaging modality, including second contouring data generated by a second human participant on the one or more second image datasets, the one or more second image datasets not overlapping with images in the one or more first image datasets;

auto-contour the first one or more first image datasets and the second one or more image datasets, using a computer-implemented autosegmentation engine to generate participant-specific computational reference contours third contouring data generated by the autosegmentation engine without requiring human contouring and without requiring identical or overlapping first and second image datasets, wherein the computational reference contours for each participant are generated from a participant's respective image datasets;

compare contouring by the first human participant to contouring by the second human participant by:

comparing the first contouring data generated by the first human participant to the participant-specific computational reference contours of the third contouring data for the first human participant generated by the autosegmentation engine to generate first comparison data:

comparing the second contouring data generated by the second human participant to the participant-specific computational reference contours of the third contouring data for the second human participant generated by the autosegmentation engine to generate second comparison data; and performing a transitive analysis comparison of the first human participant to the second human participant by separately analyze the first comparison data and the second comparison data relative to a common reference provided by the third contouring data generated by the autosegmentation engine;

generate an indication of one or more systemic differences between contouring by the first and second human participants based on the transitive analysis; and display, on a user interface, the indication of the one or more systemic differences, wherein the indication includes visually distinguishable representations of missing, extra, and common volumes.

* * * * *